(12) United States Patent
Morel et al.

(10) Patent No.: US 9,359,615 B2
(45) Date of Patent: Jun. 7, 2016

(54) PREFORMED DEFENSE IN PLANTS

(75) Inventors: Jean-Benoit Morel, Montpellier (FR); Francois Torney, Beaumont (FR); Stephane Lafarge, La Roche Blanche (FR)

(73) Assignee: GENOPLANTE-VALOR, Paris (FR)

( * ) Notice: Subject to any disclaimer, the term of this patent is extended or adjusted under 35 U.S.C. 154(b) by 448 days.

(21) Appl. No.: 13/809,062

(22) PCT Filed: Jul. 8, 2011

(86) PCT No.: PCT/EP2011/061692
§ 371 (c)(1),
(2), (4) Date: Jun. 4, 2013

(87) PCT Pub. No.: WO2012/004401
PCT Pub. Date: Jan. 12, 2012

(65) Prior Publication Data
US 2013/0326729 A1    Dec. 5, 2013

Related U.S. Application Data

(60) Provisional application No. 61/362,801, filed on Jul. 9, 2010.

(51) Int. Cl.
*C12N 15/82* (2006.01)
*C07K 14/41* (2006.01)
*C07K 14/415* (2006.01)

(52) U.S. Cl.
CPC .......... *C12N 15/8282* (2013.01); *C07K 14/415* (2013.01); *C12N 15/8279* (2013.01)

(58) Field of Classification Search
None
See application file for complete search history.

(56) References Cited

U.S. PATENT DOCUMENTS

| 2004/0123343 A1 | 6/2004 | La Rosa et al. |
| 2006/0123505 A1 | 6/2006 | Kikuchi et al. |

FOREIGN PATENT DOCUMENTS

| WO | WO 2004/013168 | 2/2004 | |
| WO | WO 2007078280 A2 * | 7/2007 | ............. C12N 15/82 |
| WO | WO 2009/156371 | 12/2009 | |

OTHER PUBLICATIONS

Friedberg (Automated protein function prediction—the genomic challenge. Brief. Bioinformatics. 7:225-242, 2006).*
Hill et al (Functional analysis of conserved histidines in ADP-glucose pyrophosphorylase from *Escherichia coli*. Biochem. Biophys. Res. Comm. 244:573-577, 1998).*
Guo et al (Protein tolerance to random amino acid change, Proc. Natl. Acad. Sci. USA 101:9205-9210, 2004).*
Matsumoto et al (Database ID Q10N98_ORYSJ. The map-based sequence of the rice genome. Nature 436:793-800, 2005).*
Vergne et al (Early and specific gene expression triggered by rice resistance gene Pi33 in response to infection by ACE1 avirulent blast fungus. New Phytologist. 174: 159-171, 2007).*
Coca et al (Enhanced resistance to the rice blast fungus Magnaporthe grisea conferred by expression of a cecropin A gene in transgenic rice. Planta. 223: 392-406, 2006).*
Database Geneseq [Online], "Rice cDNA-encoded protein SEQ ID NO. 32346" Accession No. AQD38487, Jun. 12, 2008, XP-002665753, pp. 1-2.
Database Geneseq [Online], "Oryza sativa amino acid sequence SEQ ID NO. 144000" Accession No. ANM29999, Dec. 28, 2007, XP-002665754, pp. 1-2.
Van Son, L. et al. "The BURP domain protein AtUSPL1 of *Arabidopsis thaliana* is destined to the protein storage vacuoles and overexpression of the cognate gene distorts seed development" *Plant Mol Biol*, 2009, pp. 319-329, vol. 71.
Ballini, E. et al. "A Genome-Wide Meta-Analysis of Rice Blast Resistance Genes and Quantitative Trait Loci Provides New Insights into Partial and Complete Resistance" *Molecular Plant-Microbe Interactions*, 2008, pp. 859-868, vol. 21, No. 7.
Vergne, E. et al. "ARCHIPELAGO: A Dedicated Resource for Exploiting Past, Present and Future Genomic Data on Disease Resistance Regulation in Rice" *Molecular Plant-Microbe Interactions*, 2008, pp. 869-878, vol. 21, No. 7.
Vergne, E. et al. "Preformed expression of defense is a hallmark of partial resistance to rice blast fungal pathogen *Magnaporthe oryzae*" *BMC Plant Biology*, Sep. 2010, pp. 1-17, vol. 10.
Ding, X. et al. "Genome-wide identification of BURP domain-containing genes in rice reveals a gene family with diverse structures and responses to abiotic stresses" *Planta*, 2009, pp. 149-163, vol. 230.
Written Opinion in International Application No. PCT/EP2011/061692, Jan. 5, 2012, pp. 1-6.

* cited by examiner

*Primary Examiner* — Medina A Ibrahim
*Assistant Examiner* — Wayne Zhong
(74) *Attorney, Agent, or Firm* — Saliwanchik, Lloyd & Eisenschenk

(57) ABSTRACT

The present invention relates to plants having increased preformed defense, their production and uses. The invention more particularly discloses plants which overexpress a p33kD or BURP protein, or an ortholog thereof, and exhibit an increased pre-formed resistance to pathogens.

18 Claims, 20 Drawing Sheets

Figure 15

Figure 1:
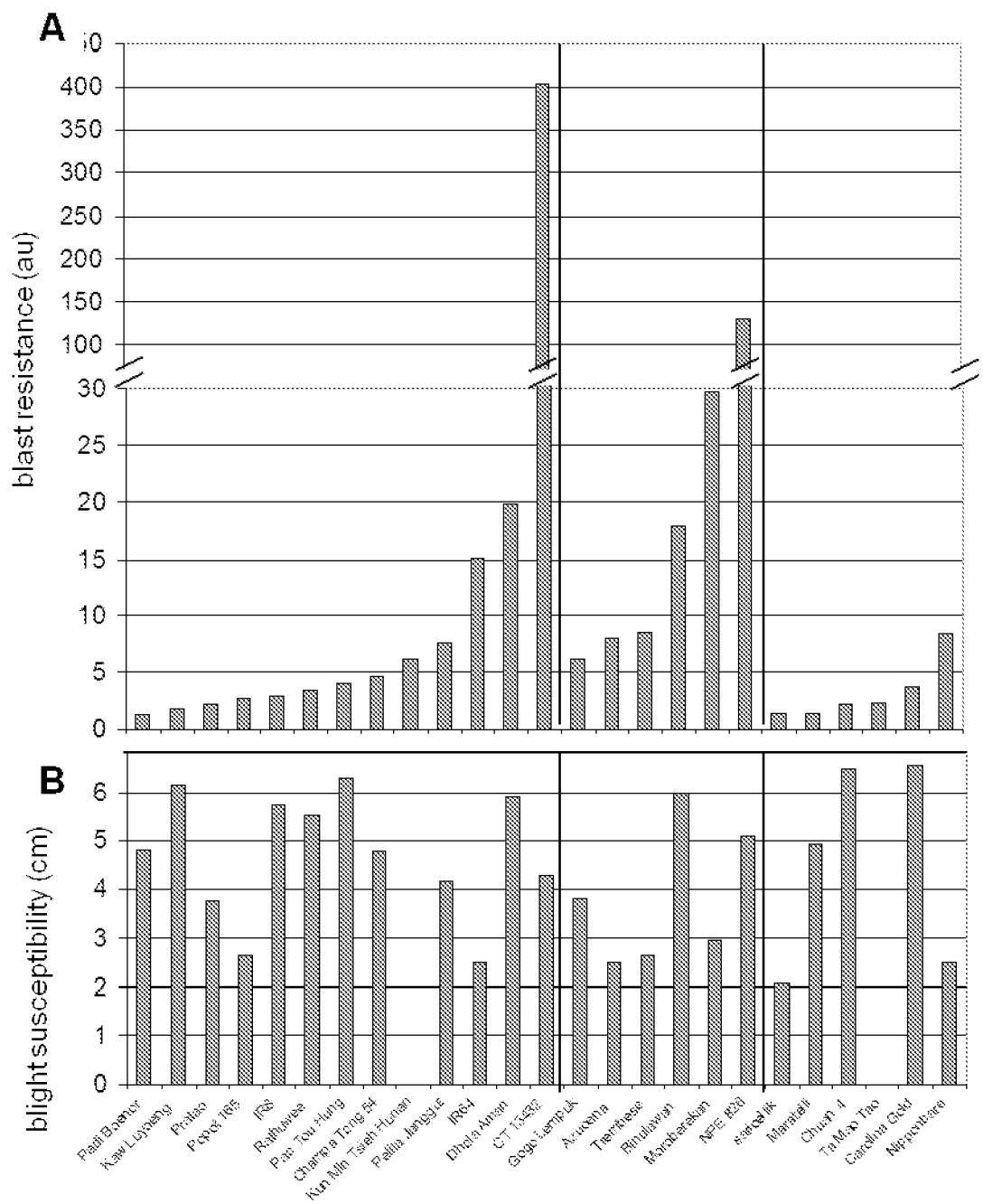

| Name | Annotation/function | Accession | Type | Differential expression upon infection | Reference |
|---|---|---|---|---|---|
| The 21 genes used for the calculation of the preofrmed expression index | | | | | |
| CEBIP | glycosylphosphatidylinositol-anchored protein 2 | Os03g04110 | Receptor | | Kaku et al, 2006 |
| EDR1 | MAPKKK | Os03g06410 | Regulator Gene | + | Kim et al, 2003 |
| EDS5 | mate transporter | Os02g02960 | Regulator Gene | + | Nawrath et al, 2002 |
| HLHDB | putative helix-loop-helix DNA-binding protein | Os03g53020 | Regulator Gene | - | Vergne et al, 2008 |
| MAPK6 | MAPK | Os05g49140 | Regulator Gene | -/+ | Vergne et al, 2008 |
| SPL7 | heat stress transcription factor | Os05g45410 | Regulator Gene | + | Yamanouchi et al, 2002 |
| ZnFg1 | Zinc finger, C3HC4 type (RING finger) | Os06g43210 | Regulator Gene | + | Vergne et al, 2008 |
| ZnFgXS | XS Zinc finger transcription factor | Os12g09580 | Regulator Gene | + | Vergne et al, 2008 |
| EIN2 | polycistin cation channel protein | Os07g06300 | Regulator Gene | ? | Jun et la, 2004 |
| 33KDA | 33 kDa secretory protein | Os03g16950 | Defense Gene | + | Vergne et al, 2007 |
| BURP | BURP domain | Os05g12640 | Defense Gene | -/+ | Vergne et al, 2008 |
| CHI | chitinase | Os07g35560 | Defense Gene | + | Vergne et al, 2007 |
| GLUC | Glucan endo-1,3-beta-glucosidase | Os01g71340 | Defense Gene | + | Vergne et al, 2008 |
| PBZ1 | PR10 family | Os12g36880 | Defense Gene | + | Midoh et al, 1996 |
| POX223 | peroxidase | Os07g48020 | Defense Gene | + | Vergne et al, 2007 |
| SUB | subtilase family protein | Os01g58290 | Defense Gene | + | Vergne et al, 2007 |
| PR5 | PR5 family | Os12g43360 | Defense Gene | + | Rakwal et al, 2001 |
| RBBI2 | PR6 family | Os01g03390 | Defense Gene | na | Qu et la, 2003 |
| GNS1 | PR2 family | Os05g31140 | Defense Gene | na | Jwa et al, 2006 |
| LTP2 | lipid transfer protein precursor | Os11g02369 | Defense Gene | ? | Cheng et al, 2004 |
| OsKS4 | 9b-pimara-7,15-diene synthase | Os04g10060 | Defense Gene | ? | Shimura et la, 2007 |
| Other genes used | | | | | |
| ZnFg2 | Zinc finger, C3HC4 type (RING finger) | Os06g03580 | Regulator Gene | + | Vergne et al, 2007 |
| HSP90 | Hsp90 protein | Os06g50300 | Regulator Gene | + | Vergne et al, 2007 |
| NPR1 | disease regulator | Os01g09800 | Regulator Gene | + | Chern et al, 2005 |
| RCI1 | lipoxygenase | Os12g37260 | Regulator Gene | + | Schaffrath et al, 2000 |
| ACTIN | actin | Os03g50890 | Control | na | - |

Figure 16

| Gene | CT13432 | IR36 | Moroberekan | Padi Boenor | Nipponbare | Maratelli | Mean | SD | VC |
|---|---|---|---|---|---|---|---|---|---|
| Actine | 96 | 93 | 93 | 100 | 97 | 105 | 97.4 | 4.9 | 5.0 |
| 33KDA | 134 | 136 | 118 | - | 160 | 186 | 146.6 | 26.7 | 18.2 |
| BURP | 128 | 125 | 101 | 104 | 96 | 119 | 112.1 | 13.8 | 12.3 |
| CHI | 133 | 142 | 95 | 114 | 102 | 96 | 113.6 | 19.8 | 17.4 |
| HLHDB | 104 | 97 | 113 | 104 | 103 | 109 | 105.0 | 5.5 | 5.2 |
| HSP90 | 84 | 115 | - | 125 | 122 | 119 | 113.1 | 15.1 | 13.3 |
| PBZ1 | 103 | 109 | 97 | 92 | 115 | 96 | 101.9 | 8.6 | 8.5 |
| SPL7 | 112 | 126 | 121 | 127 | 111 | 111 | 118.1 | 7.7 | 6.5 |
| ZnFg2 | 136 | 136 | 114 | 126 | 123 | 128 | 127.2 | 8.6 | 6.7 |

Figure 17

|  | gene expression values | | normalized expression values | | | |
| --- | --- | --- | --- | --- | --- | --- |
|  | POX223 | CHI | POX223 | CHI |  | index expression |
| Pratao | 1.07E-001 | 5.64E-002 | 0.21 | 0.12 |  |  |
| Chuan 4 | 2.50E-001 | 3.35E-001 | 0.49 | 0.68 |  |  |
| Padi Boenor | 6.17E-002 | 3.37E-002 | 0.12 | 0.07 |  |  |
| Kaw Luyoeng | 5.81E-002 | 1.64E-001 | 0.11 | 0.33 |  |  |
| IR8 | 5.63E-002 | 4.81E-002 | 0.11 | 0.10 |  |  |
| Popot 165 | 7.33E-002 | 4.30E-002 | 0.14 | 0.09 |  |  |
| Maratelli | 1.55E-001 | 1.75E-001 | 0.30 | 0.36 |  |  |
| sariceltik | 1.16E-001 | 1.71E-001 | 0.23 | 0.35 |  | mean |
| Kun Min Tsieh Hunan | 2.36E-001 | 2.60E-001 | 0.46 | 0.53 |  |  |
| Pao Tou Hung | 2.52E-001 | 2.84E-001 | 0.49 | 0.58 |  |  |
| Champa Tong 54 | 2.88E-001 | 3.08E-001 | 0.56 | 0.63 |  |  |
| Pelita Janggut | 2.29E-001 | 1.01E-001 | 0.45 | 0.21 |  |  |
| Carolina Gold | 4.73E-001 | 5.24E-001 | 0.93 | 1.07 |  |  |
| Dhola Aman | 2.63E-001 | 3.61E-001 | 0.52 | 0.74 |  |  |
| IR64 | 5.44E-001 | 1.94E-001 | 1.06 | 0.40 |  |  |
| Binulawan | 1.14E+000 | 8.26E-001 | 2.22 | 1.69 |  |  |
| Azucena | 1.74E+000 | 1.32E+000 | 3.41 | 2.69 |  |  |
| Trembese | 1.14E+000 | 1.31E+000 | 2.24 | 2.68 |  |  |
| Gogo Lempuk | 3.64E-001 | 4.70E-001 | 0.71 | 0.96 |  |  |
| Moroberekan | 2.09E+000 | 1.17E+000 | 4.08 | 2.38 |  |  |
| Nipponbare | 6.63E-001 | 3.98E-001 | 1.30 | 0.81 |  |  |
| Rathuwee | 1.19E-001 | 6.56E-002 | 0.23 | 0.13 |  |  |
| mean | 5.11E-001 | 4.90E-001 | 1.00 | 1.00 |  |  |

Figure 18

|  | Constitutive expression | | | | Differential expression upon infection[c] | | | |
|---|---|---|---|---|---|---|---|---|
|  | japonica | | indica | | japonica | | indica | |
| Gene | P value[a] | Effect on resistance[b] | P value[a] | Effect on resistance[b] | early | late | early | late |
| PBZ1 | 0.02* | + | 0.02* | + | + | + | nc | + |
| BURP | 0.0006*** | + | nt | NL | nc | + | + | nc |
| HSP90 | 0.04* | + | 0.16 | + | + | + | nc | + |
| GLUC | 0.03* | + | 0.24 | - | + | + | + | + |
| SPL7 | 0.76 | + | 0.02* | + | + | + | + | nc |
| POX223 | 0.06 | + | 0.19 | - | nc | + | nc | + |
| ZnFg2 | 0.12 | + | 0.87 | + | nc | + | nc | + |
| NPR1 | 0.24 | + | 0.94 | + | + | + | + | + |
| CHI | 0.26 | + | 0.87 | + | + | nc | nc | nc |
| 33KDA | 0.67 | + | 0.39 | + | nt | nt | nt | nt |
| PR5 | 0.67 | + | nt | NL | + | + | + | + |
| SUB | nt | NL | 0.29 | + | + | + | + | + |
| RBBI2 | nt | NL | 0.29 | - | nc | + | + | + |
| EDR1 | nt | NL | 0.31 | + | nt | nt | nt | nt |
| CEBIP | nt | NL | 0.31 | + | nc | + | nc | + |
| OsKS4 | nt | NL | 0.36 | + | nt | nt | nt | nt |
| HLHDB | nt | NL | 0.55 | - | - | - | - | nc |
| EIN2 | nt | NL | 0.94 | + | nt | nt | nt | nt |
| RCI1 | nt | NL | 0.95 | - | nt | nt | nt | nt |
| GNS1 | nt | NL | 0.99 | + | nc | + | nc | + |
| EDS5 | nt | NL | nt | NL | nc | nc | + | + |
| MAPK6 | nt | NL | nt | NL | nt | nt | nt | nt |
| LTP2 | nt | NL | nt | NL | + | + | + | nc |
| ZnFgXS | nt | NL | nt | NL | + | + | + | + |
| ZnFg1 | nt | NL | nt | NL | nc | + | nc | + |

Figure 20

|       |            | Primers Sequence |   |
| Gene  | Accession  | F | R |
|-------|------------|---|---|
| ACTIN | Os03g50890 | GCGTGGACAAAGTTTTCAACC | TCTGGTACCCTCATCAGGCATC |
| BURP  | Os05g12640 | CGGCTGGCTATCATGTTATCATCG | AGTTGGTTTATTTCGGGACAGAGG |
| PBZ1  | Os12g36880 | CCTGCCGAATACGCCTAAGATG | AGAACACATTCAGACTTGCCTCTC |
| PR5   | Os12g43380 | CGCTGCCCCGACGCTTAC | GACGACTTGGTAGTTGCTGTTGC |
| GLUC  | Os01g71340 | CGTTCCATATATAGTTGTGGTTTG | TCAAGTTCATATTATTTGTCTCTG |
| POX223| Os07g48020 | ACGACGCCCAACGCCTTC | CTTCCAGCAACGAACGCATCC |
| SPL7  | Os05g45410 | CGGATTAGAGGCTTGCGTGTTAC | GCACAGTAGTCAGCGGATAGAAC |
| CHI   | Os07g35560 | CCAGACGGGACGGAGGTTTAC | AGATGCGTGTGCGACCAAGG |
| 33KDA | Os03g16950 | GCCACCACTGACATGACCAAG | ACGCTGAAACATCCACAGACAC |
| NPR1  | Os01g09800 | CCTGATGGTTGCCTTCTGTC | ATTCAAGCACTTGTATTACACCTC |
| HSP90 | Os06g50300 | CCTCCTCCTCCTCCTCCTCAC | GGACACCTCAGCCTGGAACTC |
| SUB   | Os01g58290 | CGGAAAGTTGCTGACCCATTCG | GCTCGCCGCACCTTGATTG |
| EDS5  | Os02g02980 | CACGGCTAGGTTCAGTTCCAATG | CCAATCCATCAGCAAGAAGAGACG |
| EDR1  | Os03g06410 | ATGGGTGGACCTGTGAAAGATGC | AGTAGGGCACGGTGACGAGAC |
| CEBIP | Os03g04110 | CACTTGTACGGCTGCTTGAA | GGAAGGTGGGAAGTCCATTC |
| RCI1  | Os12g37260 | CAATTTGAGTTGTGCCAATGAGC | CTGTGTTAGCCATTCCTTGACG |
| RBBI2 | Os01g03390 | ATCTGTGTCCGTCAATAAAACTCG | TTGCTCTTGGTCACTGGCTAG |
| MAPK6 | Os05g49140 | GCCGTTCAATATGGTGTTTCAAG | GCCTTATATCTGGGTGGATGGG |
| GNS1  | Os05g31140 | CAGAGGGCTTGGCTTGCG | GCCTACCACAGCGTACCG |
| LTP2  | Os11g02369 | GACATCGCAGGCCGTACAT | CATGCATCGATCTAGCAGCAA |
| HLHDB | Os03g53020 | GGTTTTGAAACATGATCCTGCTG | AGGTACATTGACAAGGAGATATGG |
| ZnFg1 | Os06g43210 | GCGGTGTTGTATGTAGCTGGT | GTCTCAGCGTACGGTTCACA |
| ZnFgXS| Os12g09560 | TGAGTGATGACTATGATTCTGATG | TTCTCTGTGACGCTTGACC |
| ZnFg2 | Os08g03580 | CTGCGTACCCTCTCCATCTGA | TGGCAGCCTCTTCGTTGTT |
| OsKS4 | Os04g10060 | TACGGTTGGTTGTTAGAGAAGACG | CCATTCATAGCACCCATCATTTCC |
| EIN2  | Os07g06300 | GCAACAAGGAACCAGTGACAACC | GCAGTCGTCTCCGCAGTTAGG |

Figure 21

| chromosome | cM | Marker | eQTL | QTL | eQTL_LOD BURP_1 | BURP_2 | CHI_1 | CHI_2 | resistance QTL_LOD R_1 | R_2 |
|---|---|---|---|---|---|---|---|---|---|---|
| 1 | 75,3 | RG345 | eBURP | | 11.56 ** | 12.67 *** | 1.44 | 1.62 | 0.25 | 0.46 |
| 1 | 232,1 | RG612 | | 1Q1 | 4.27 * | 0.01 | 0.71 | 1.48 | 19.18 **** | 25.16 **** |
| 4 | 0,0 | RG476A* | | 4Q1 | 0.80 | 0.80 | 0.00 | 4.22 * | 9.65 ** | 17.53 *** |
| 7 | 0,0 | RG351 | eCHI | 7Q1 | 2.79 | 0.70 | 4.41 * | 6.39 | 10.79 ** | 9.53 ** |
| 7 | 46,9 | RG4 | eBURP+eCHI | | 17.12 *** | 10.69 ** | 9.19 ** | 4.72 * | 0.90 | 0.27 |
| 7 | 145,1 | RG528A | | 7Q2 | 0.51 | 1.27 | 0.19 | 0.67 | 17.06 *** | 15.08 *** |
| 10 | 40,8 | RG257 | | 10Q1 | 0.51 | 0.68 | 0.02 | 0.04 | 6.22 * | 9.29 ** |
| 11 | 109,1 | RG103A | eBURP+eCHI | 11Q3 | 12.78 *** | 0.06 | 4.98 * | 6.15 * | 6.47 * | 9.19 ** |
| 11 | 0,0 | RG109ALT | | 11Q1 | 3.25 | 0.04 | 0.13 | 1.01 | 7.37 * | 13.52 *** |
| 11 | 115,7 | RG16 | | 11Q2 | 1.98 | 1.54 | 1.76 | 0.83 | 9.03 ** | 12.83 *** |
| 12 | 0,0 | RG323 | | 12Q1 | 4.67 * | 0.03 | 0.93 | 1.47 | 34.75 ****** | 31.16 *** |
| 12 | 15,1 | RG543 | | 12Q1 | 0.06 | 2.76 | 2.18 | 0.07 | 14.77 *** | 13.49 *** |
| 12 | 32,9 | RG869A | | 12Q2 | 0.11 | 1.55 | 0.29 | 0.03 | 12.80 *** | 9.27 ** |
| 12 | 51,9 | cdo344 | | 12Q3 | 0.28 | 1.10 | 3.80 | 0.58 | 11.26 ** | 10.35 ** |

Figure 22

PREFORMED DEFENSE IN PLANTS

CROSS-REFERENCE TO RELATED APPLICATIONS

This application is the U.S. national stage application of International Patent Application No. PCT/EP2011/061692, filed Jul. 8, 2011, which claims the benefit of U.S. Provisional Patent Application No. 61/362,801, filed Jul. 9, 2010, the disclosures of which are hereby incorporated by reference in their entireties, including all figures, tables and amino acid or nucleic acid sequences.

The Sequence Listing for this application is labeled "29I3767.txt" which was created on Jun. 2, 2013 and is 24 KB. The entire contents of the sequence listing is incorporated herein by reference in its entirety.

The present invention relates to plants having increased pre-formed defense, their production and uses.

BACKGROUND

Plants are constantly exposed to microbial attacks and have developed sophisticated systems to counteract them. Plants respond to infection using a two-branched innate immune system [1]: a first branch, called basal resistance, responds to pathogen-associated molecular patterns (PAMPs). Basal resistance is thought to be the default defense system that allows limited restriction of pathogen growth. A second branch, called gene-for-gene resistance, responds to pathogen virulence factors. Both basal and the gene-for-gene induced resistances can be divided into three steps.

In a first step, the plant throughout different recognition systems detects PAMP or virulence effectors of the pathogen; these recognition systems involve pattern recognition receptors (PRRs) for basal resistance and resistance (R) genes for gene-for-gene resistance [1, 2]. In rice, the transmembrane glycoprotein CEBiP is the best-characterized example of PRR for basal resistance to the fungal pathogen *Magnaporthe oryzae* [3]. There is little polymorphism in the case of PRR and in the molecular pattern that they recognize. The gene-for-gene recognition system is much more polymorphic. Depending on the presence/absence of the R genes and of the corresponding pathogen molecule, the interaction will be incompatible (plant is resistant) or compatible (plant is susceptible).

In a second step, signal transduction occurs and requires regulators such as MAP kinases [4] and transcription factors [5]. These genes that are here collectively called defense regulators are often conserved across species; for example NPR1 is a central regulator in both Monocots and Dicots [6, 7, 8, 9, 10]. Many of these regulator genes are differentially expressed during infection [11, 12].

In a third step, defense responses are induced. These include production of antimicrobial secondary metabolites (phytoalexins) [13], pathogenesis-related (PR) proteins (e.g. chitinases, glucanases) [14, 15], cell-wall strengthening [16] and programmed cell death, leading to the Hypersensitive Response (HR) [17]. The genes that act downstream of the regulators controlling the disease resistance pathways are collectively called defense genes and are typically transcriptionally regulated upon infection.

Besides these mechanisms explaining how resistance is built, breeders and biologists use an agnostic but operational term for a phenomenon found in many plant species: partial resistance. Partial resistance is first characterized by quantitative limitation of pathogen growth. In rice, partial resistance to the blast fungus *M. oryzae* is often divided into two main values: the number and the size of lesions [18]. Another characteristic of partial resistance is that it is controlled by the plant development and usually increases with aging [19]. Rice is a good model to study partial resistance as breeders have extensively used it, through the identification of quantitative trait loci (QTL). There is a considerable amount of genetic data available that was recently reviewed [18]. More than 340 QTL have been identified and summarized to 165 metaQTLs. Further analysis lead to the identification of an operational set of about 20 genomic areas. Importantly, this large set of genetic data could be compared to the large set of information available on R gene analogs, regulators and defense genes in rice [12, 18]. This analysis showed that, on a global scale, R gene analogs are often found in intervals defining metaQTLs [18]. This was an expected finding consistent with the hypothesis that partial resistance is due, in part, to defective R genes that recognize with low efficiency pathogens and trigger weak defense response. Less expected was the finding that regulator and some defense genes were also significantly associated with metaQTLs [12]. Finally, partial resistance has long been considered as a durable form of resistance. This may be due to the fact that the low levels of resistance conferred by partial resistance do not impose strong selection pressure for the pathogens. This may also be due to particular mechanisms that cannot be easily broken down by pathogens.

Preformed, constitutive, physical and chemical barriers likely play a role in partial resistance by limiting the growth of a normally virulent pathogen. They involve cuticle [20] and cell wall strengthening [21] and represent mostly broad-spectrum pathogen resistance. In rice, like in other plants, silicon accumulation plays direct and indirect role in partial resistance [22]. Antimicrobial molecules, called phytoanticipins, can also accumulate before infection [23]. Although there is a large body of evidence that defense genes, especially pathogenesis-related (PR) proteins, are constitutively expressed in uninfected tissues [15], there is no indication of the effect of their level of expression before infection on resistance. In contrast, there are many indications that the over-production of PR proteins confers resistance [24, 25], that mutations in genes negatively regulating disease resistance can increase defense gene expression [e.g. 26, 27] or that over-expression of regulator genes acting positively on disease resistance can increase defense gene expression [e.g. 28]. Thus there are indirect evidences that constitutive expression of regulator and defense genes could participate to plant pathogen resistance.

To face pathogen attacks, plants could use a proactive strategy of constitutive expression of inducible defense systems. Recently, large-scale expression studies across *Arabidopsis thaliana* cultivars have been completed and showed that gene expression greatly vary from one genotype to another [29]. Interestingly, the 2,200 differentially expressed genes were significantly enriched for genes classified as controlling biotic and abiotic responses [29]. Thus these classes of genes seem to display high expression level polymorphism (ELP). However, there is little information of a possible link between these ELPs and biological traits. ELP of major R genes can obviously explain the polymorphism in the disease resistance pathway [30, 31]. In these cases, the presence/absence of the resistant R allele explains the ELP and the corresponding resistance/susceptibility phenotypes. In the case of partial resistance, there is no evidence that plants show ELPs of the surveillance receptors and/or regulator and defense systems. Our hypothesis is that such expression level polymorphism for receptors, regulator and defense genes belonging to plant disease resistance pathways play a role in partial resistance.

We wanted to test the hypothesis that, besides inducible defense systems, rice has developed a proactive strategy to face its major fungal pathogen, *M. oryzae*. For this purpose, we looked for possible links between constitutive levels of expression of genes markers of the disease resistance pathways (thereafter called defense-related genes) in relation to partial resistance. We show that constitutive expression of defense-related genes shows high ELP and likely plays a central role in partial resistance to *M. oryzae*. Thus we identify a possible mechanism underlying a phenomenon that has been known and used for a long time with no comprehensive knowledge of what was behind.

SUMMARY OF THE INVENTION

The invention relates to a plant which overexpresses (e.g., constitutively expresses) a p33 kD or BURP protein, or an ortholog thereof, and exhibits an increased pre-formed resistance to pathogens.

In a particular embodiment, said overexpression of p33 kD or BURP, or an ortholog thereof, is caused or induced by:

(a) selection of plants expressing p33 kD or BURP constitutively, or (b) induction of the p33 kD or BURP gene promoter into the plant; or (c) introduction into the plant, or a cell or ancestor thereof, of an expression cassette comprising a nucleic acid encoding p33 kD or BURP or its ortholog.

The invention also relates to seeds of the plant of the invention.

A further aspect of the invention relates to a plant, or a descendant of a plant grown or otherwise derived from said seeds.

The invention also concerns a method for producing a plant having increased preformed resistance to pathogens, wherein the method comprises the following steps:

(a) introducing into a cell of said plant a nucleic acid construct comprising a nucleic acid sequence encoding a p33 kD or BURP protein, or an ortholog thereof, under the control of a constitutive promoter enabling the expression of said nucleic acid sequence;

(b) optionally, selection of plant cells of step (b) which express p33 kD or BURP, or an ortholog thereof;

(c) regeneration of plants from cells of step (a) or (b); and (d) optionally, selection of a plant of (d) with increased resistance to pathogens.

A further object of the invention resides in a method for selecting a plant having preformed resistance to pathogens, the method comprising determining whether a plant, or a cell thereof, expresses one or more proteins selected from p33 kD, BURP, PBZ1, PR3, POX223, CHI, GLUC and SPL7, said expression being an indication that the plant exhibits preformed resistance. Preferably, the protein is selected from p33 kD and BURP.

The invention may be used in any plant, preferably a cereal, more preferably selected from rice, wheat, barley, oat, rye, sorghum or maize. It may be used to create or select plants having improved preformed resistance against a variety of pathogens, including without limitation *Magnaporthe, Puccinia, Aspergillus, Ustilago, Rhizoctonia, Septoria, Erisyphe* and *Fusarium* species, in particular *Magnaporthe oryzae.*

A further aspect of the invention is a recombinant nucleic acid comprising a nucleic acid sequence encoding a p33 kD or BURP protein, or an ortholog thereof, operably linked to a promoter functional in a plant. In a particular embodiment, the promoter is a constitutive plant promoter, a plant tissue-specific promoter, a plant development-stage-specific promoter, an inducible promoters or a viral promoter.

The invention also relates to a recombinant vector comprising the expression cassette, a cell or plant transformed with the recombinant vector, as well as seeds of such a plant.

The invention also resides in a method of identifying a molecule that increases preformed resistance in a plant, the method comprising determining whether a test molecule increases expression of a protein selected from p33 kD and BURP.

A further object of the invention is the use of a molecule that increases p33 kD or BURP gene expression for increasing preformed resistance of plants to pathogens.

The invention also relates to a method for conferring or increasing preformed resistance to pathogens in a plant, comprising a step of inducing or stimulating the expression of p33 kD or BURP in said plant.

LEGENDS TO THE FIGURES

FIG. 1. Partial Resistance to Blast and Bacterial Blight (A) Partial resistance to blast fungus (*Magnaporthe oryzae*) was calculated according to fungal mass as measured by Q-PCR (see Methods and FIG. 15). Three multivirulent isolates were used. The genotypes are displayed from the most susceptible to the most resistant. (B) Partial resistance to bacterial blight (*Xanthomonas oryzae* pv *oryzae* PX099) was estimated 15 days after inoculation and quantified by measuring the length of chlorosis from the inoculation section. The different rice sub-groups are separated by vertical bars (indica, tropical japonica and temperate japonica cultivars from left to right).

FIG. 2. Variability of Defense Induction Across Rice Diversity

Expression given in arbitrary unit (au) was measured by QRT-PCR before inoculation (TO) and 1, 2, 3 and 4 day(s) post inoculation (dpi) with the CD203 *M. oryzae* isolate in two or three biological repetitions. The expression of four genes is shown: POX223 (A), RBBI2 (B), PBZ1 (C) and BURP (D). Moroberekan is a tropical japonica cultivar that shows strong partial resistance. Nipponbare and Maratelli are temperate japonica cultivars that show respectively strong and weak partial resistance and IR64 and Padi Boenor are indica cultivars that show respectively strong and weak partial resistance.

FIG. 3. Constitutive and Inducible Expression of Defense Genes

The expression of the 21 genes was measured before and after inoculation with the *M. oryzae* isolate CD203 and compared to partial resistance index (A) as measured in FIG. 1. A gene expression index (B), integrating all 21 gene expression values for each condition, was calculated as indicated in FIG. 17. Partial resistance and gene expression indexes correlate before infection (0 dpi) but not after (1 to 4 dpi).

FIG. 4. Constitutive Expression of Defense Systems Across Rice Diversity

The gene expression values before infection of 21 genes of 23 rice cultivars (IND=indica, JTROP=tropical japonica, JTEMP=temperate japonica) were used for hierarchical clustering using GenePattern analysis platform (http://www.broadinstitute.org/cancer/software/genepattern/index.html). Pearson correlation was used as distance and a pairwise complete-linkage as clustering method for both genes and varieties. Bootstrap values were estimated on 1000 permutations by the approximately unbiased method using R package pvclust [57]. Only bootstrap values above 95 are shown. Each point represents the mean of three independent experiments. Most of the tropical japonica cultivars show a distinct expression pattern as compared to the other cultivars. The regulons are indicated by roman numbers.

Figure 5:
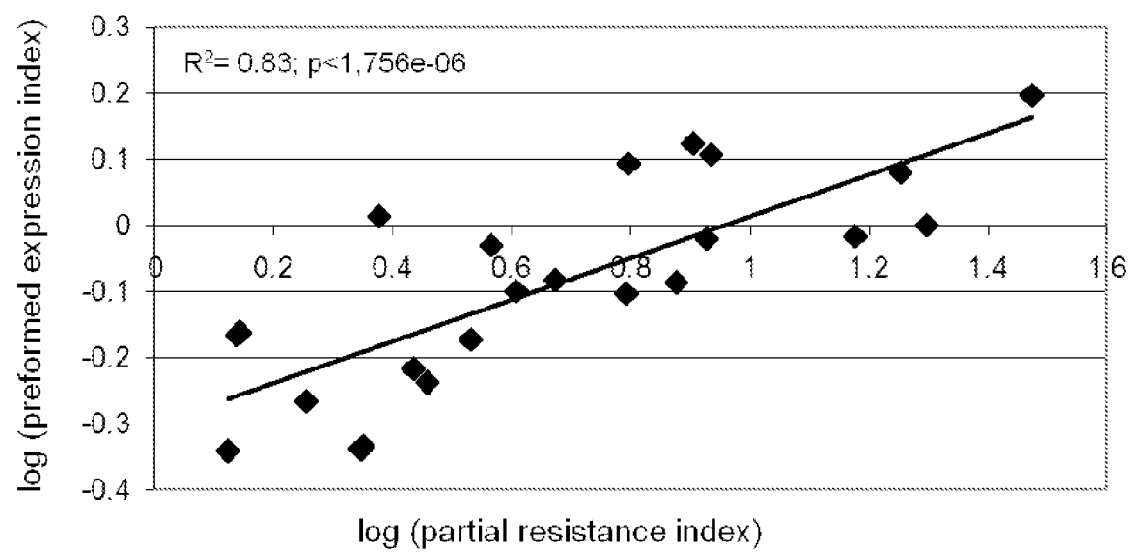

FIG. 5. Partial Resistance and Constitutive Expression of Defense Correlate

The log value of partial resistance (X-axis) and expression of preformed expression of 21 genes (Y-axis) indexes of the 23 representative rice cultivars was plotted. Correlation coefficients were statistically tested using the Pearsons' product moment correlation coefficient test and the Bonferroni correction (the initial 0.01 threshold was divided by 3 because each data set was tested 3 times).

Figure 6:
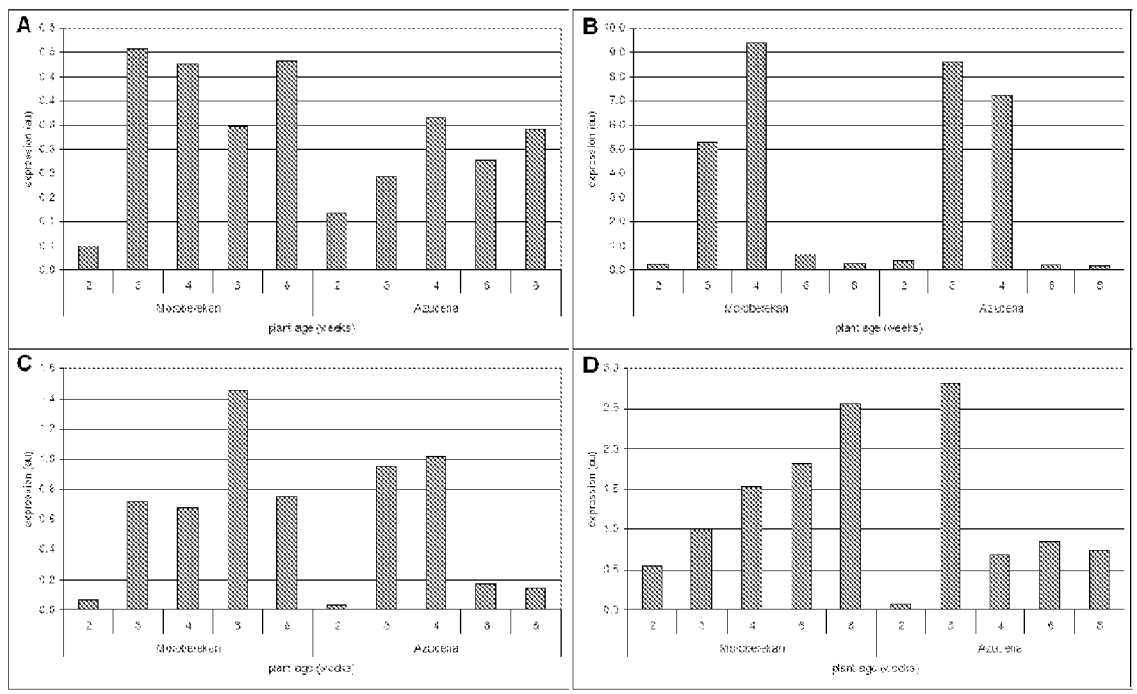

FIG. 6. Developmental Control of Preformed Expression of Defense in Tropical Japonica Rice The last leaves of plants at different developmental stages (2 to 8 weeks) were simultaneously harvested and analyzed for preformed expression of defense. Two tropical japonica cultivars (Moroberekan and Azucena) were selected as representative of cultivars showing high preformed expression of defense. The example of four genes is shown: POX223 (A), RBBI2 (B), PBZ1 (C), SPL7 (D) and similar results were found with four other genes (data not shown).

Figure 7:
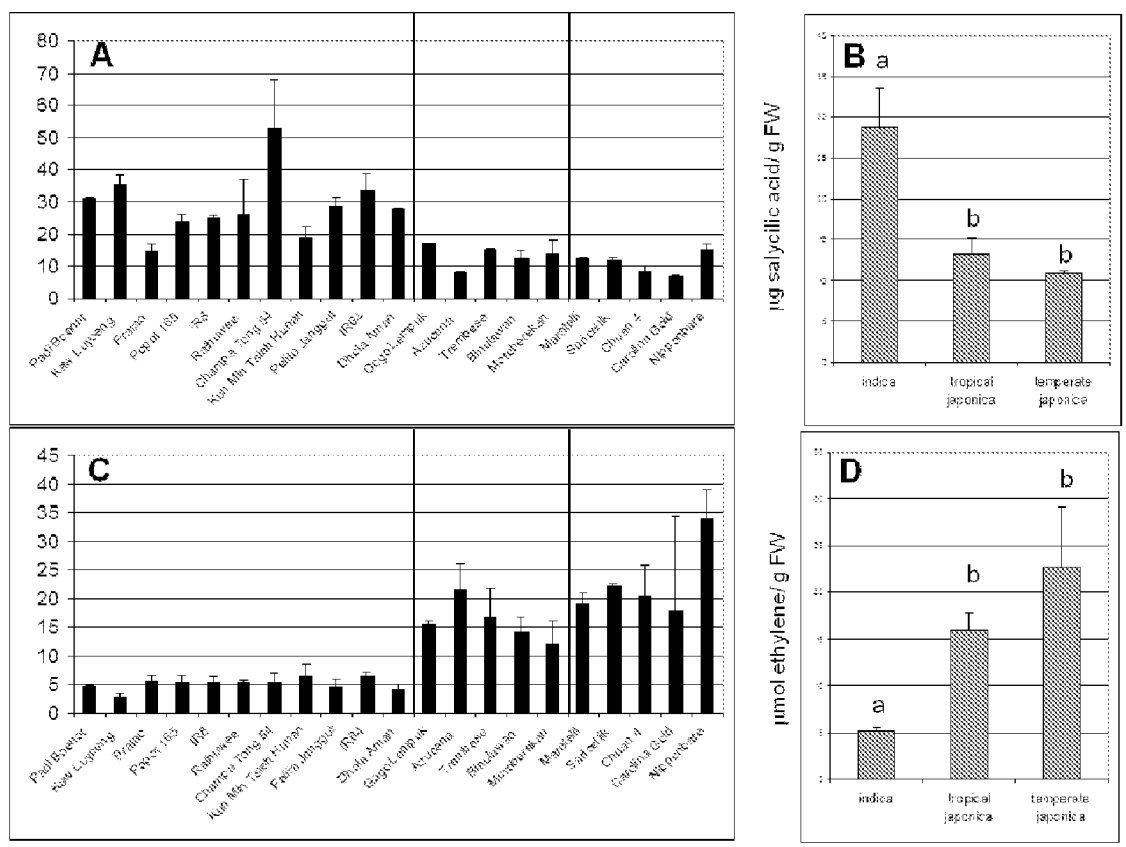

FIG. 7. Preformed quantities of salyeiliesalicylic acid and ethylene in rice cultivars.

Constitutive amounts of salicylic acid (A) and ethylene (C) were measured in the absence of infection. Each point represents the mean and standard deviation of two separate assays. The vertical lines separate, from left to right, indica, tropical japonica and temperate japonica genotypes. For each sub-group, the cultivars are displayed from the less to the more resistant. The average values in the different rice sub-groups are also shown for salicylic acid (B) and ethylene (D). The letters (a or b) above the bars indicate whether the average value of salicylic acid levels (B) or ethylene levels (D) are significantly different between each sub-groups as evaluated by a Student tests ($P<0.005$).

Figure 8:
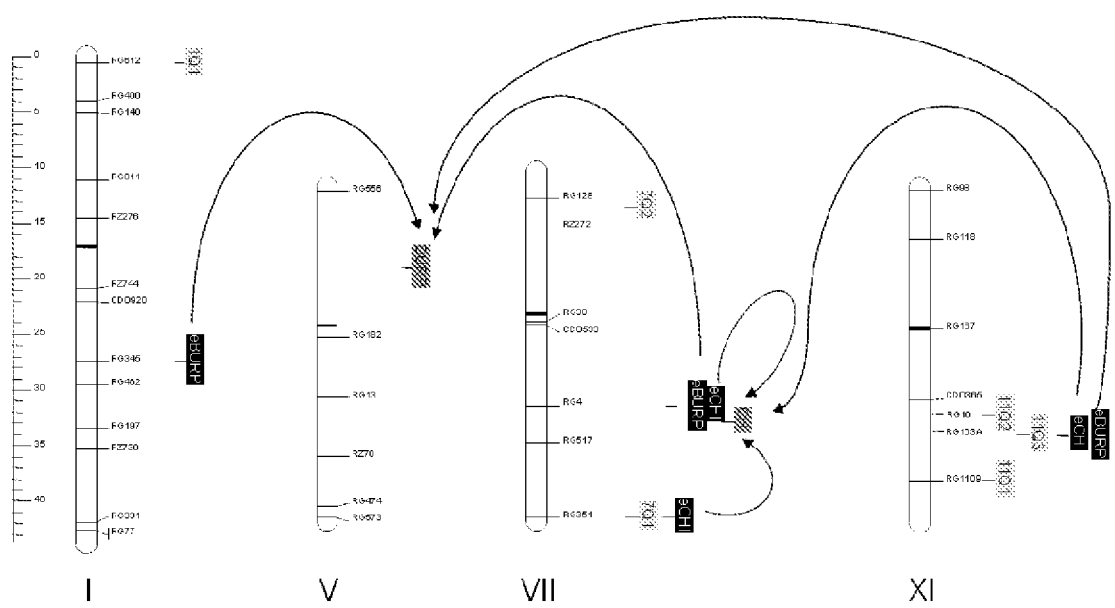

FIG. 8. Simplified QTL and eQTL Maps for Blast Disease Resistance and Constitutive Expression.

QTLs (towards CD203 isolate) are indicated in light grey squares, eQTLs (for the structural genes BURP and CHI) in black boxes and structural genes in dark grey boxes. The arrows indicate the positive effects of eQTLs on structural genes. Genetic markers used for QTL analysis are indicated on the right of each chromosome. Only chromosomes showing significant eQTLs (LOD score>3) are shown. This map was obtained using the Moroberekan X Co39 RILs population; similar results were obtained using the IR64 X Azucena population (data not shown).

Figure 9:
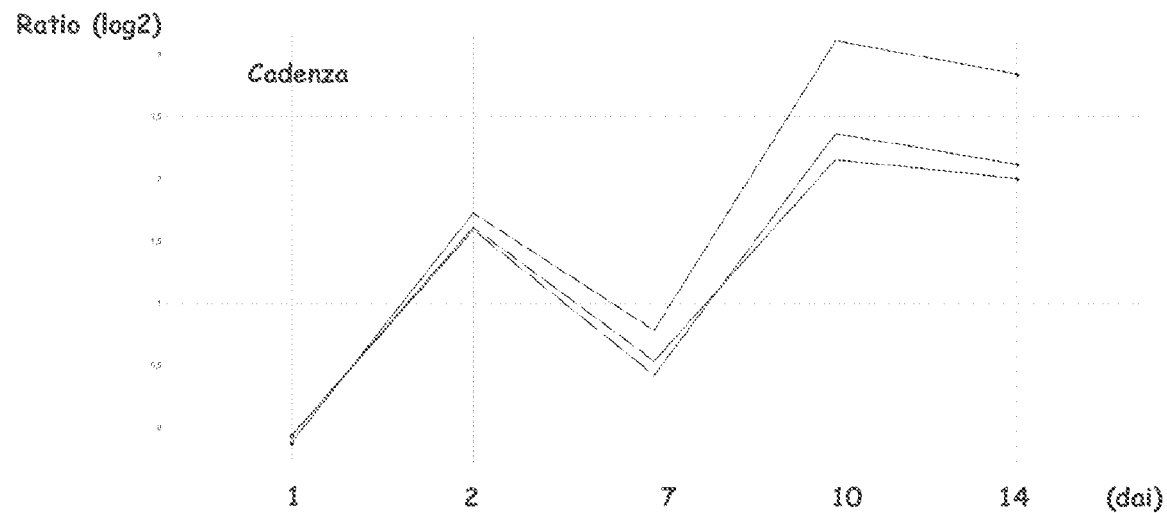

FIG. 9: kinetic (five points) of p33 KD expression with the three Affymetrix probes in avirulent conditions for Cadenza genotype. X axis: number of days after infection, Y axis: ratio expression infected plants/expression control plants (value in log radix 2: a value of one corresponds to a factor two variation of the expression).

Figure 10:
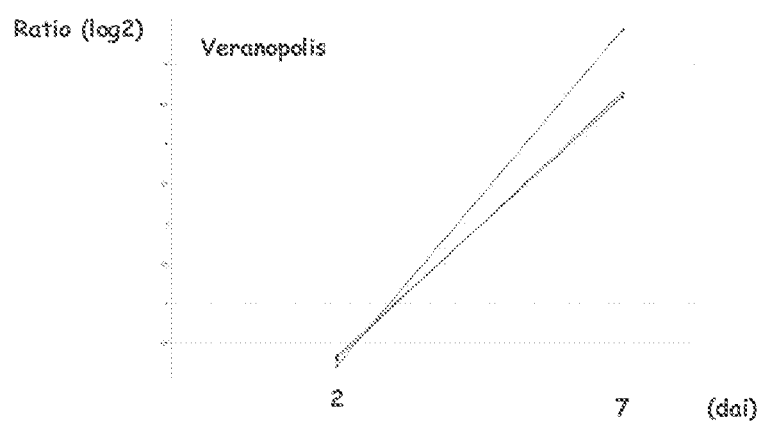

FIG. 10: kinetic (two points) of p33 KD expression with the three Affymetrix probes in avirulent conditions for Veranopolis genotype. X axis: number of days after infection, Y axis: ratio expression infected plants/expression control plants (value in log radix 2: a value of one corresponds to a factor two variation of the expression).

Figure 11:
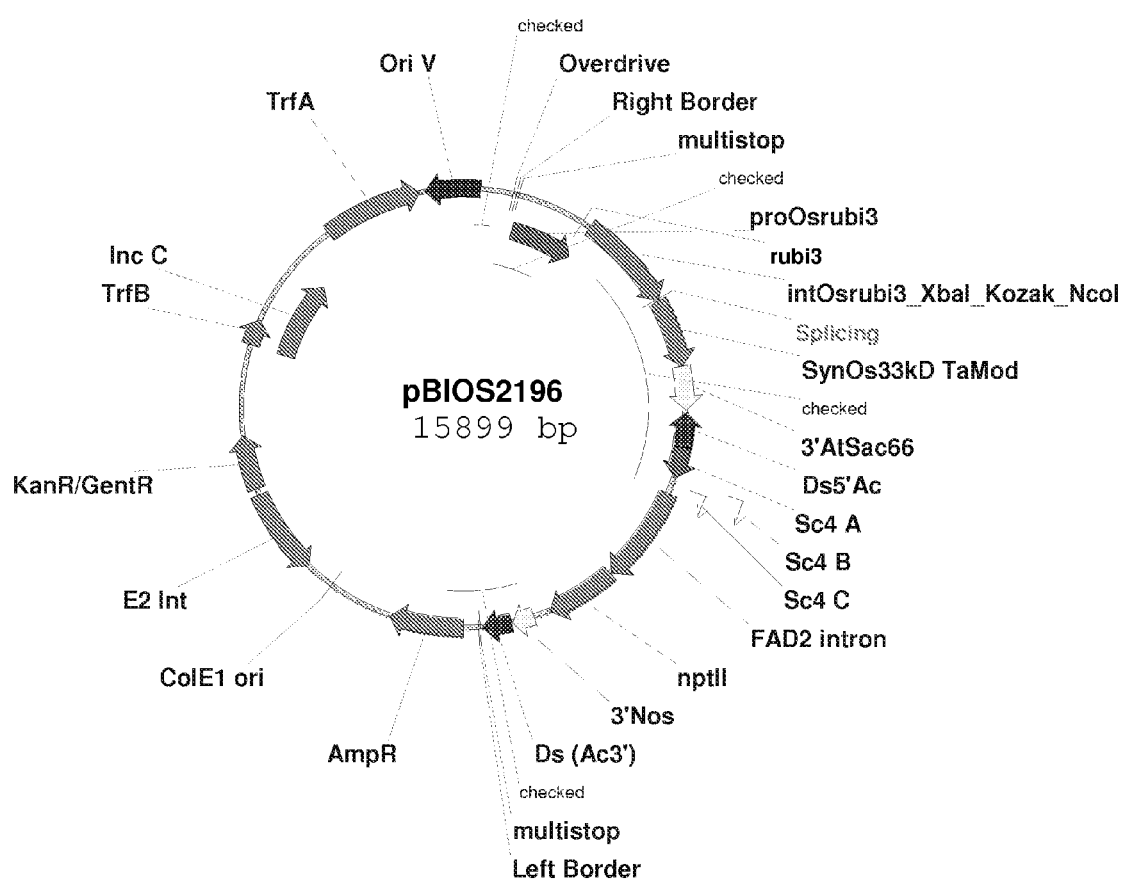

FIG. 11: Map of plasmid pBIOS2196.

Figure 12:
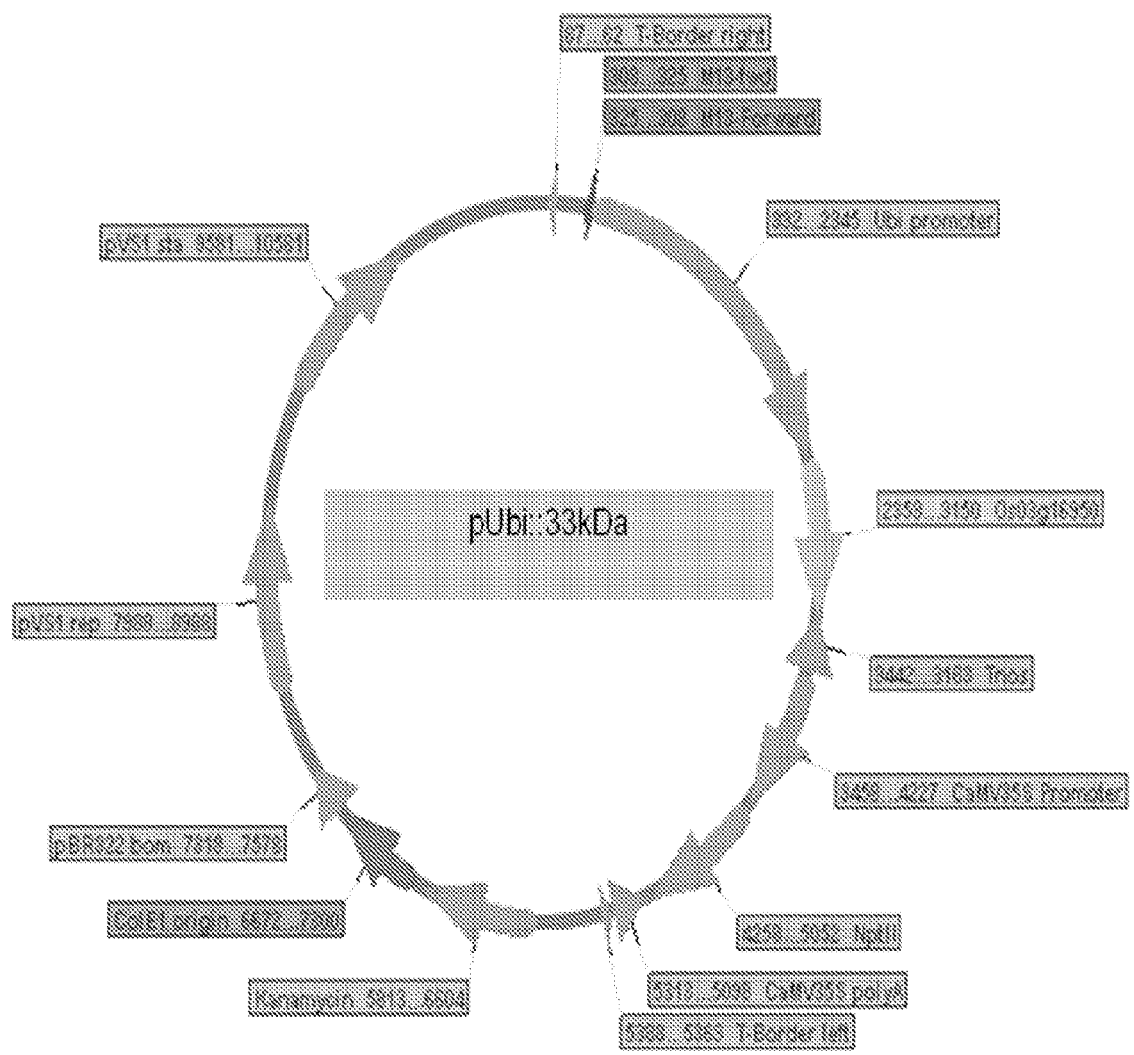

FIG. 12: Map of plasmid pUbi::33 kDa.

Figure 13:
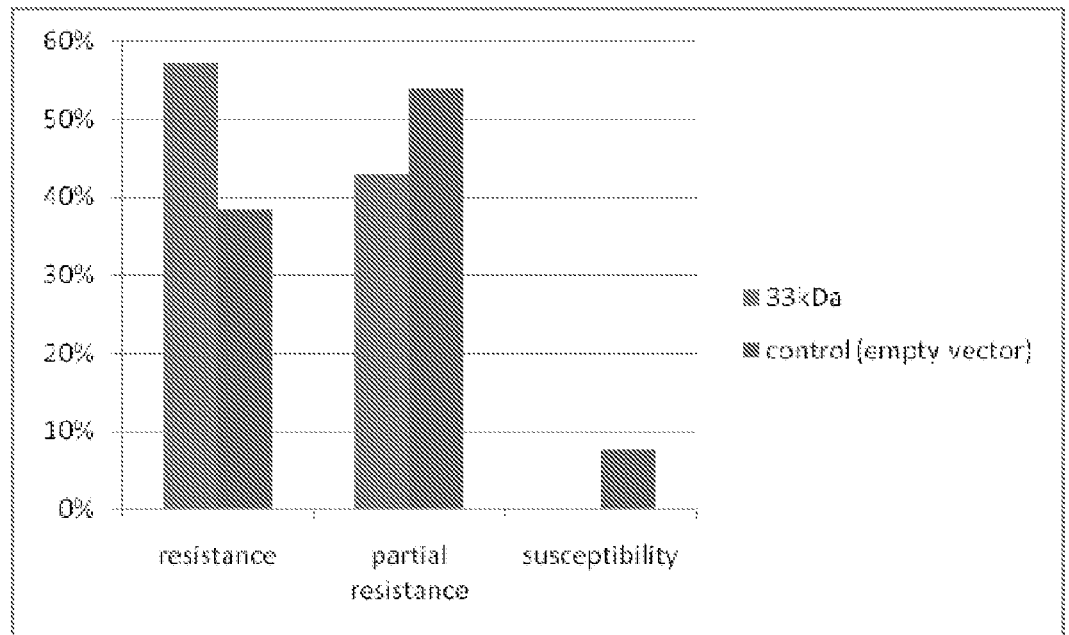

FIG. 13: Transgenic plant expressing p33 KD are more resistant.

Figure 14:
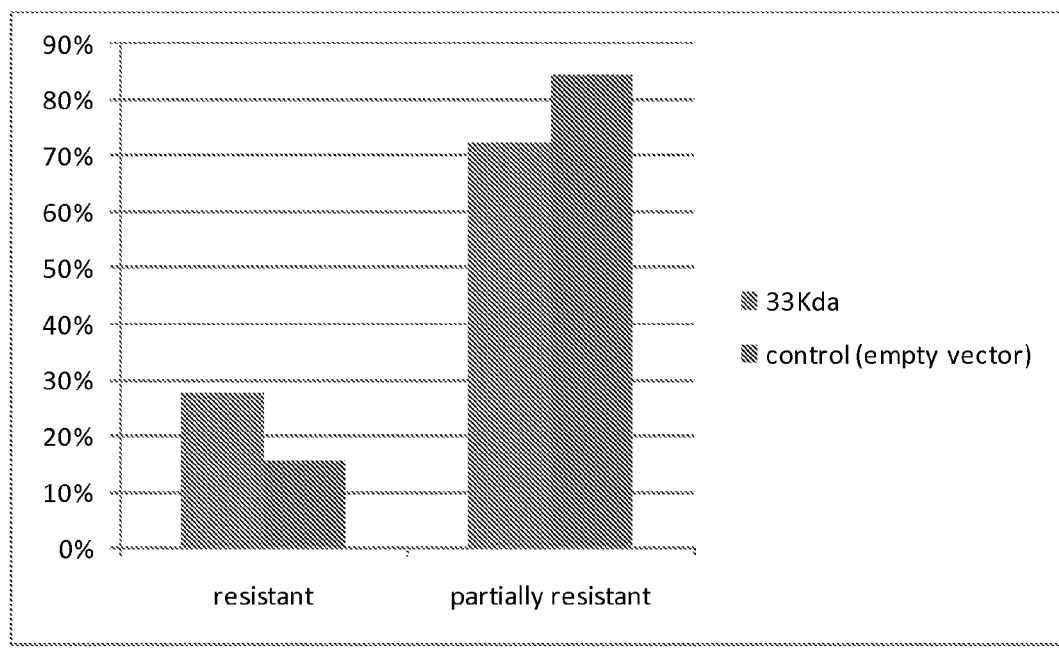

FIG. 14: Transgenic plant expressing p33 KD are more resistant.

Figure 15:
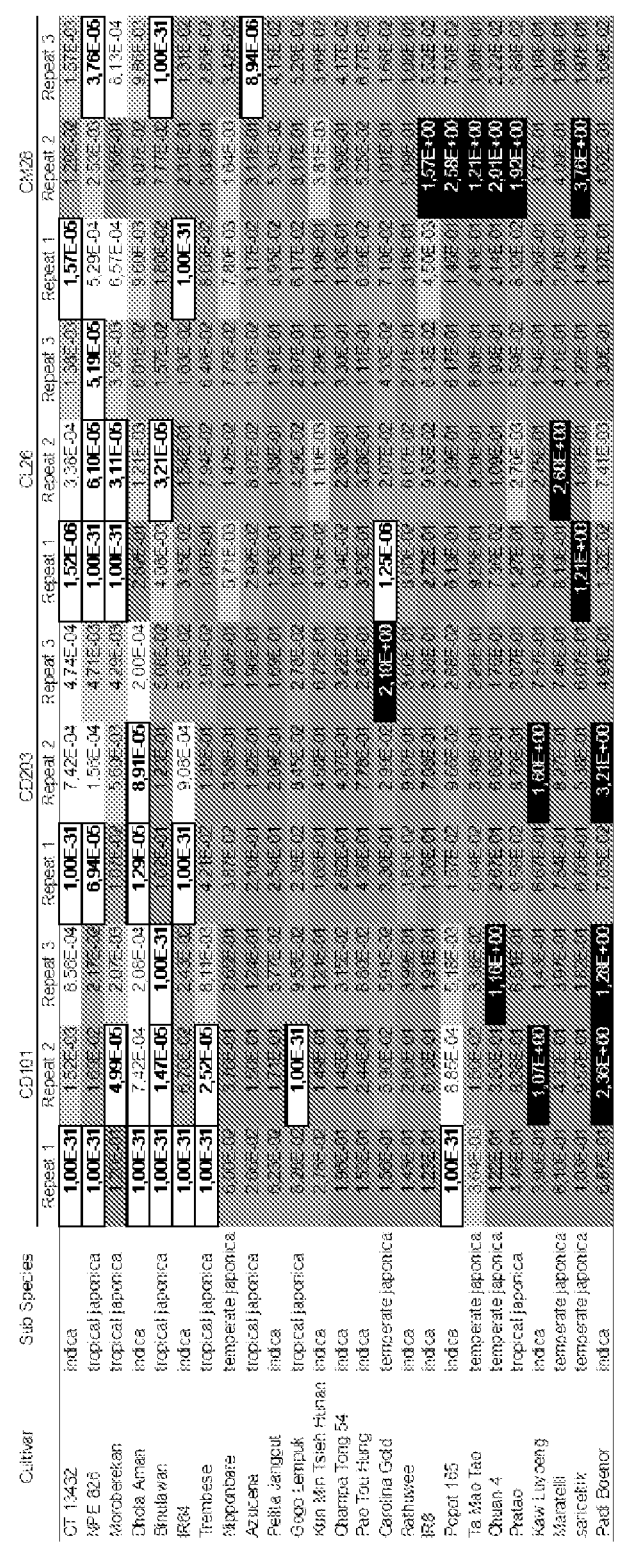

FIG. 15. List of Cultivars Characterized for their Basal Resistance to Blast Disease Twenty-eight cultivars were initially characterized, 13 Indica cultivars, eight tropical Japonica cultivars and seven temperate Japonica cultivars. The quantity of four isolates of M. oryzae (CD101, CD203, CL26, CM28) were measured by Q-PCR in planta 7 dpi in three biological repetitions. The darker the color is, the more the fungus is present. The inverse of the mean of the 12 measures obtained for each cultivar was used as an estimation of partial resistance. Measures lower than 1.00E-05 (black frame) were removed of the calculation because considered as measures of complete resistance.

FIG. 16. List of Genes

FIG. 17. QRT-PCR amplification efficiency of selected primer pairs across rice diversity FIG. 18. Index of Gene Expression Level Example of calculation of gene expression index. Three steps were used for the calculation of the preformed defense index:

1—For each gene, the mean is calculated for the 23 cultivars;
2—the expression value for each gene in each cultivar is then divided by the mean expression level; and
3—for each cultivar, the mean for the 21 genes selected is calculated.

Figure 19:
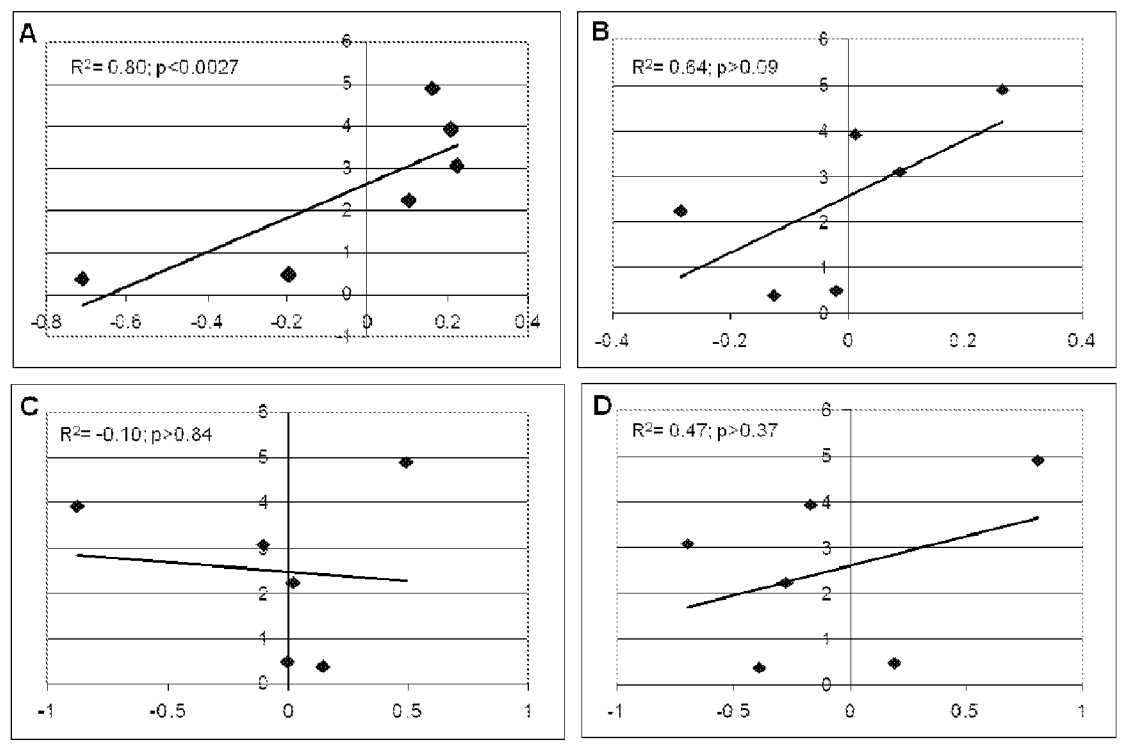

FIG. 19. Correlation Between Partial Resistance and Constitutive or Inducible Expression of Defense Genes The log value of partial resistance index (Y-axis) and expression of preformed expression of 21 genes index (X-axis) of the six representative rice cultivars (FIG. 3) was plotted for each time point before (A) and during infection (1 dpi: B, 2 dpi: C and 3 dpi:D). Correlation coefficients were statistically tested using the Pearsons' product moment correlation coefficient test.

FIG. 20. ANOVA Analysis of Preformed Expression of Defense a: The model of the ANOVA test was <<M. oryzae quantity after inoculation=constitutive expression of gene 1+constitutive expression of gene 2+ . . . constitutive expression of gene X+residual>>.

b: correlation value between constitutive expression of each gene and basal resistance as estimated by PCA. When there was no apparent possible correlation in the PCA analysis (NL: no link), the test was not done (nt: not tested).

c: Early time points in the kinetic are 1 and 2 dpi, late time points are 3 and 4 dpi. +: Induction; −: repression; NC: no change in the expression. The CD203 isolate of M. oryzae was used.

FIG. 21: List of nucleic acid Primers (SEQ ID NOs: 10-61)

FIG. 22. LOD Score and Position of the QTL and eQTL

Resistance (R) was evaluated as well as the expression, before infection, of the BURP and CHI genes (eQTL) using the Moroberekan X Co39 mapping population. The QTLs and eQTLs were detected using the MapDisto software. Two replicates were done; the LOD score is indicated for each position and character.

DETAILED DESCRIPTION

Partial resistance to plant pathogens is extensively used in breeding programs since it could contribute to resistance durability. Partial resistance often builds up during plant development and confers quantitative and usually broad-spectrum resistance. However, very little is known on the mechanisms underlying partial resistance. Partial resistance is often explained by poorly effective induction of plant defense systems. By exploring rice natural diversity, we asked whether expression of defense systems before infection could explain partial resistance towards the major fungal pathogen Magnaporthe oryzae. The constitutive expression of 21 defense-related genes belonging to the defense system was monitored in 23 randomly sampled plants for which partial resistance was measured. We identified a strong correlation between the expression of p33 kD or BURP before infection and partial resistance. Increasing constitutive expression of these genes also correlated with the establishment of partial resistance during plant development. These results indicate that constitutive expression of p33 kD or BURP can cause, stimulate or maintain resistance in plants. The finding of this preformed defense system allows development of new plants having improved properties.

DEFINITIONS AND GENERAL METHODS

The term "pre

Arabido
(SEQ ID NO: 4)
mktivvkcfl llalvcscra adsiwqlcnt nsnisassqv sknidsllat lvsktpskgf ktttsssynn kekvyglaqc rgdisntdcs tciqdaakki revcqnqsds rilydfcflr ysqenfigkl dtgagliyfn vanvteidpk kfdnelgalf dkirseavlp knkglgkgkt kltpfvtlng lvqctrdlse ldcaqcfata vgsfmttchn kkgcrvlyss cyvryefypf yfpldpaktg psvgrissvh lsp maize
(SEQ ID NO: 5)
parent_transcript = GRMZM2G043878_T01; parent_gene = GRMZM2G043878|Zea mays|AA|268
MESSRMRCCMLLVVSLALLLPLGMAADSIGSYCSGSSYAGSSKAVANINSVLADLVASASSTGGYA

TSTAGKGNNSIIYGLAQCRGDVSASDCASCLADAAKQLPSTCSYSSDARIWYDYCFMRYENANFFG

QADTDAGVILVNVQAMDNPKAFEKAVGKVMGKATAQASAAGSAGLGRDKEQYTPFVSIYGLAQCTR

DLAPLTCAQCLSTALSRFGDYCGAQQGCQINYSSCRVRYEIYPFYFPLAGKGGGLATTDMTKNTKI

VVRP

Sorghum
(SEQ ID NO: 6)
MGMIHTPYTMKFSTMRCCVLLVSLALLPLGMAADSIGSYCSGSRYAGSNKAVTSINSVLADLVATASTG

GGYATSTAGKGNNIIYGLAQCRGDVSASDCAACLADAAKQLPSTCSYSSDARIWYDYCFMRYENADFFG

QADTGAGVILVNVQAMDNPKAFEKAVGKVIGKATAQASAAGSAGLGRDKDQYTPFVSIYGLAQCTRDLA

PLTCAQCLSTAVSRFGDYCGAQQGCQINYSSCRVRYEIYPFYFPLAGNGGAGGRATTDMTKNTKIIVHP

Barley
(SEQ ID NO: 7)
MALCRARSGLLLVAMALLPLGMAMDAIGSNCAGTRYAAGSGKGNIDSVLADLVAKGSSGGFATSIAGKG

NSTVVYGLAQCRGDVSASDCSACLVDAAKQLPAACSYLSDAIIWYDFCFMRYDNTDFVGHSDTGAGVIL

VNVQAADDPKPFKTAVGKVMNKATAKSSASGSAGLGRSKYQYTPFVTIYGLAQCTRDLAPLACAQCVSV

ALSKFGDYCGAQQGCQINYSSCRVRYEIYPFYFPLDGAANGRATTDMTKYTKIVVHA

These proteins represent further particular objects of the present invention.

In a preferred embodiment, the invention relates to constructs and plants containing or expressing a p33 kD protein comprising SEQ ID NO:2 or a sequence having a degree of sequence identity with SEQ ID NO: 2 superior to 65%.

Within the context of the present invention, the term "pathogens" designates all pathogens of plants in general. More preferably the pathogens are fungal pathogens. In a particular embodiment, fungal pathogens are cereal fungal pathogens. Examples of such pathogens include, without limitation, *Magnaporthe, Puccinia, Aspergillus, Ustilago, Rhizoctonia, Septoria, Erisyphe* and *Fusarium* species. In the most preferred embodiment, the pathogen is *Magnaporthe oryzae*. The invention is particularly suited to create rice resistant to *Magnaporthe*.

A promoter is "heterologous" to a gene when said promoter is not naturally associated to said gene. A heterologous promoter may be natural, synthetic, recombinant, hybrid, etc. It may be of cellular or viral origin. The heterologous promoter is preferably a strong and/or constitutive promoter. Constitutive promoters may include, for example CaMV 35S promoter (Odell et al. (1985) Nature 313, 9810-812), rice actin promoter (McElroy et al. (1990) Plant Cell 2: 163-171) and ubiquitin promoter (Christian et al. (1989) Plant Mol. Biol. 18 (675-689); pEMU (Last et al. (1991) Theor Appl. Genet. 81: 581-588); MAS (Velten et al. (1984) EMBO J. 3. 2723-2730); ALS promoter (U.S. application Ser. No. 08/409,297), and the like.

Non-limitative examples of constitutive promoters that are commonly used are the cauliflower mosaic virus (CaMV) 35S promoter, the nopaline synthase (Nos) promoter, the Cassava vein Mosaic Virus (CsVMV) promoter (Verdaguer et al., 1996), the rice actin promoter followed by the rice actin intron (RAP-RAI) contained in the plasmid pAct1-F4 (McElroy et al., 1991), the corn ubiquitin or rice ubiquitin 3 promoter (SIVAMANI et QU, Plant Mol Biol., 60:225-239, 2006).

Non-limitative examples of organ or tissue specific promoters that can be used in the present invention include for instance root specific promoter like pPRO110 from rice, the kernel specific promoter High Molecular Weight (HMW) promoter (Thomas and Flavell, 1990), or the leaf specific promoters as pPEPc promoter (Jeanneau et al., 2002), or the Rubisco small subunit promoter (rbcS) (Katayama et al., 2000) which is specific of the bundle-sheath.

Inducible promoters include for instance pathogene responsive or drought stress responsive promoters, such as the rd29A promoter which comprises a dehydration-responsive element (Kasuga et al., 1999; Narusaka et al., 2003), or the senescence specific SAG12 promoter (Noh and Amasino, 1999).

Within the context of this invention, the term "overexpressed" or "overexpression" indicates either an increase in the level of active protein present in the cell or plant and/or a modified expression profile of a protein, such as a constitutive expression.

Generation of Plants that Overexpress p33 kD or BURP Overexpression may be obtained by techniques known per se in the art such as, without limitation, by genetic means, enzymatic techniques, chemical methods, or combinations thereof. Overexpression may be conducted at the level of DNA, mRNA or protein, and induce the expression (e.g., transcription or translation) or the activity of the protein. A preferred overexpression method affects expression and leads to the increased production of a functional protein in the cells. It should be noted that the induction may be transient or permanent. Preferably, an overexpression designates an increase by at least 10%, preferably at least 20%, more preferably at least 30% or even more, as compared to reference expression or to an average value.

In a first embodiment, overexpression is induced by a mutation in the coding gene, for example point mutation, deletion, insertion and/or substitution of one or more nucleotides in a DNA sequence. This may be performed by techniques known per se in the art, such as e.g., site-specific mutagenesis, ethyl methanesulfonate (EMS) mutagenesis, targeting induced local lesions in genomes (TILLING), homologous recombination, conjugation, etc. A particular approach is gene overexpression by insertion a DNA sequence through transposon mutagenesis using mobile genetic elements called transposons, which may be of natural or artificial origin.

Mutations may also be introduced within the sequence of the promoter. Mutations in the coding sequence may result in gain of function by increasing biological activity and efficacy of the protein. Alternatively, introducing mutations into the promoter sequence may result in gain of function by induction of the promoter activity by controlling and enhancing transcription of the gene.

In a particular embodiment, overexpression is induced by introduction into a plant of an expression cassette comprising a nucleic acid sequence coding for the protein under control of a promoter enabling the expression of said nucleic acid sequence.

Overexpression may also be performed transiently, e.g., by applying (e.g., spraying) an exogenous agent to the plant, for example molecules that induce the protein expression or activity.

A preferred overexpression is a constitutive expression under control of a constitutive promoter.

Another preferred overexpression results from successive plant selections steps.

A nucleic acid molecule may be introduced into a plant cell by any means, including transfection, transformation, transduction, electroporation, particle bombardment, agroinfection, etc. In a preferred embodiment, a nucleic acid molecule is introduced via *Agrobacterium* transformation using the Ti plasmid as described e.g., by Toki et al. (2006).

A variety of techniques for genetic transformation of plant cells or plants are available in the art. By way of non-limitative examples, one can mention methods of direct transfer of genes such as direct micro-injection into plant embryoids, vacuum infiltration (Bechtold et al. 1993) or electroporation (Chupeau et al., 1989) or the bombardment by gun of particles covered with the plasmidic DNA of interest (Fromm et al., 1990; Finer et al., 1992). *Agrobacterium* mediated transformation methods may also be used such as *Agrobacterium tumefaciens*, in particular according to the method described in the article by An et al. (1986), or *Agrobacterium rhizogenes*, in particular according to the method described in the article by Guerche et al., (1987). According to a particular embodiment, it is possible to use the method described by Ishida et al. (1996) for the transformation of maize. According to another embodiment, the wheat is transformed according to the method described in International Application WO 00/63398.

According to the present invention, the introduced nucleic acid molecule may be maintained in the plant cell stably. Alternatively, the introduced nucleic acid molecule may be transiently expressed or transiently active.

Selection of a plant which overexpress a p33 kD or BURP protein can be made by techniques known per se to the skilled person (e.g., PCR, hybridization, use of a selectable marker gene, protein dosing, western blot, etc.).

Plant generation from the modified cells can be obtained using methods known per se to the skilled worker. In particular, it is possible to induce, from callus cultures or other undifferentiated cell biomasses, the formation of shoots and roots. The plantlets thus obtained can be planted out and used for cultivation. Methods for regenerating plants from cells are described, for example, by Fennell et al. (1992) Plant Cell Rep. 11: 567-570; Stoeger et al (1995) Plant Cell Rep. 14: 273-278; Jahne et al. (1994) Theor. Appl. Genet. 89: 525-533.

The resulting plants can be bred and hybridized according to techniques known in the art. Preferably, two or more generations should be grown in order to ensure that the genotype or phenotype is stable and hereditary.

Selection of plants having an increased resistance to a pathogen can be done by applying the pathogen to the plant, determining resistance and comparing to a wild type plant. Within the context of this invention, the term "increased" resistance to pathogen means a resistance superior to that of a control plant such as a wild type plant, to which the method of the invention has not been applied. The "increased" resistance also designates a reduced, weakened or prevented manifestation of the disease symptoms provoked by a pathogen.

The terms "wheat plant" and "wheat plant cell" as used herein, include any plant of plant cell of the genus *Triticum*, preferably of the species *Triticum aestivum* L. (bread wheat).

The invention also comprises host cells containing a recombinant DNA construct of the invention. These host cells can be prokaryotic cells or eukaryotic cells, in particular plant cells, and preferably maize cells.

The invention also comprises wheat plants genetically transformed by a recombinant DNA construct of the invention, and overexpressing a p33 KD or BURP or an ortholog as defined above. In said transgenic plants a DNA construct of the invention is comprised in a transgene stably integrated in the plant genome, so that it is passed onto successive plant generations. Thus the transgenic wheat plants of the invention include not only the plants resulting from the initial transgenesis, but also their descendants, as far as they contain a recombinant DNA construct of the invention. The overexpression of a p33 KD or BURP as defined above in said plants provides them an improved grain filling, when compared with a plant devoid of said transgene(s).

The invention also comprises a transgenic wheat plant, obtainable by a method of the invention, overexpressing a p33 KD or BURP as defined above.

The invention further comprises a transgenic wheat plant or an isolated organ or tissue thereof comprising, stably integrated in its genome, a recombinant expression cassette comprising a polynucleotide encoding a p33 KD or BURP as defined above.

Accordingly, the invention also encompasses isolated organs or tissues of said transgenic wheat plant (such as seeds, leafs, flowers, roots, stems, ears) containing a recombinant expression cassette of the invention.

Further aspects and advantages of the invention will be disclosed in the following experimental section, which should be considered as illustrative.

Examples

A. Methods

Rice Accessions

Rice diversity was estimated from Garris et al [53]. The names used for the rice accessions are the names used for the mini Germplasm Bank. Seeds were obtained from CIRAD-Center for Biological Resource (France). Rice was grown as in [11].

Selection of Marker Genes for Gene Expression Studies

Three types of genes along the disease resistance pathway were selected: one PRR, 12 regulators and 12 defense genes (FIG. 16). This classification of genes was sometimes arbitrary as for some genes the putative function was unknown (e.g. 33 kDA secretory protein). The role of some putative regulator genes in rice was deduced from gene expression studies (e.g. the EDS5 gene) [11] and by transcriptome information gathered in the Archipelago database [54, 12]. The NPR1 [8], RCI1 [36] and EIN2 [35] genes were included as markers for the salicylic acid, the jasmonic acid and the ethylene pathways respectively. Other genes were included in this study as regulator genes (HLHDB, ZnFg1, ZnFg2 and ZnPgXS) given their annotations and expression studies (FIG. 16). Defense genes were genes for which the annotation and expression studies suggest a direct role in limiting pathogen growth. For example the CHI gene potentially degrades chitin, the major component of fungal cell-wall. Altogether, these genes are representative of the defense arsenal. All genes used in this work were, to some extent, differentially expressed upon infection (FIG. 16).

Fungal Quantification in Planta and Evaluation of Partial Resistance

Twenty-eight cultivars were characterized for partial resistance (FIG. 15). Plants were grown and inoculated when 3-weeks old with spore suspensions of 50000 spores/mL as in [11]. The quantity of fungal mass for four isolates of *M. oryzae* (CD101, CD203, CL26, CM28) was measured by Q-PCR on DNA extracted 7 days post-inoculation, in three independent experiments (8 leaves/experiment). Fungal growth was estimated using Taqman® technology with the MAGGY transposon for *M oryzae* (MAGGY Taqman probe TGAGCAGCCAACGCCGCCACAA, SEQ ID NO: 8) and the ACTIN gene for rice (ACTIN Taqman probe ATCACGC-CCAGCAAGGTCGAGACG, SEQ ID NO: 9). Primers are given in FIG. 21. The Eurogentec Taqman kit was used on a Stratagene MX300P QPCR machine. In addition to classical symptoms (data not shown), a total of 12 values (4 isolates×3 biological replicates) were used to build the partial resistance index. The inverse of the mean of the 12 measures obtained per cultivar was assumed to be an estimation of partial resistance (FIG. 15).

Gene Expression Analysis

RNAs were extracted and gene expression measured as in [11]. All expression experiments were done two to three times in biologically independent experiments. The primers used are listed in FIG. 21. Calculation of gene expression was normalized using the rice ACTIN gene and expression formula from Pfaffl [56]. Although naturally occurring DNA polymorphism only slightly modifies gene expression using oligo-nucleotide microarrays [29], QRT-PCR that involves longer DNA sequences could be sensitive to DNA polymorphism. Thus we evaluated the variability of QRT-PCR measures for eight genes in six representative rice accessions (FIG. 17). Four genes (33 kDA, BURP, CHI and HSP90) showed QRT-PCR efficiencies more variable than in the ACTIN control but the overall variation was low (<20%). This variability was not related to indica/japonica sub-group or elevated/low partial resistance classes. The four other genes tested (PBZ1, HLHDB, SPL7 and ZnFg2) showed very limited variability across rice diversity. We concluded that the QRT-PCR conditions used in this study, although influenced by DNA polymorphism, were sufficient to evaluate expression variability across rice diversity.

Statistical Analysis of the Data

The Pearson correlation coefficient value and the test of the value being different from zero were estimated with functions "cor" and "cor.test" in R Stats package (http://www.R-project.org). For Principal Component Analysis (PCA), the numeric variables were log 2 transformed. PCA were done with function "dudi.pca" in ade4 library (http://pbil.univ-lyon1.fr/ADE-4) for R (http://www.R-project.org). For ANOVA, the variables were log 2 transformed. The ANOVA models "*M. oryzae* quantity=gene 1 expression value+gene 2 expression value+ . . . +gene x expression value" were tested with the "lm" function in R Stats package. Models were validated with Shapiro.test function (residues normality) in R Stats package and hmctest or bptest functions (heteroskedasticity) in lmtest library (http://cran.r-project.org/web/packages/lmtest/index.html) for R. Models explanation was done with the anova function of R Stats package.

Salicylic Acid and Ethylene Quantification

For SA, frozen (liquid nitrogen) leaf tissues (about 0.5 g) were ground in 0.5 ml of 90% methanol. [$^{14}C$] SA was then added (60 µl) as tracer to each tube. After centrifugation (15 min, 16000 g), the residue was extracted again with 100% methanol (0.5 ml) and, after centrifugation (15 min, 16000 g), the second supernatant was added to the first one. After a third centrifugation (10 min, 16000 g) combined supernatants were evaporated to dryness with a Speedvac (5 h, 30° C.). For each sample, the dried extract was resuspended in hot water (80° C., 0.4 ml) and HCl 12 N (0.2 ml) and incubated for 45 min at 80° C. in a water bath. After cooling, 1 ml of ether was added and after centrifugation, the organic phase was collected. A new step of phase partitioning was achieved on the aqueous phase. The two organic phases were then added and evaporated to dryness under nitrogen flux. Final samples were resuspended in 200 µl of injection buffer (10% acetonitrile, 90% sodium acetate 20 mM, pH 5.0) and 50 µl of a tenth dilution was used for injection.

Total SA was measured by fluorescence ($\lambda_{ex}$ 313 nm, $\lambda_{em}$ 405 nm) with a Nova-Pak 4-mm C-18 column (150×3.9 mm; Waters) as part of the Waters system (1525 Binary HPLC Pump, 2475 Multi λ Fluorescence Detector, 2996 Photodiode Array Detector, 717 Autosampler; Waters). Data (retention time and Area) were analyzed using Empower Pro Software (Waters). Radioactivity was determined by liquid scintillation counting of an aliquot sample. Recoveries of the internal standard [$^{14}C$] SA were between 20 and 100% and for each sample, this yield was considered in SA quantity calculation. SA quantity was calculated as followed:

(quantity of SA (ng)/fresh weight (g))=dilution factor×([{(area/SA quantity standard curve slope)×(resuspending volume/injection volume)}/yield]/fresh weight (g)).

For ethylene measurements, plants were grown under sterile conditions and leaves were harvested and weighted after two weeks. Ethylene was extracted and measured as in [35].

QTL and eQTL Identification

The MapDisto free software (http://mapdisto.free.fr/) was used for QTL and eQTL analysis. Two mapping populations were used: a population of 60 RILs between Moroberekan and Co39 [38] and another between Azucena and IR64 with 84 RILs [39]. The gene expression and disease values were log 2 transformed. The distributions of the resulting values followed a normal distribution (tested with Shapiro.test function in R Stats package; data not shown) and were used for QTL analysis.

B. Sampling Rice Diversity for Partial Resistance

The goal of this study was to try to establish possible links between the constitutive expression of defense-related genes and partial resistance. Our approach was first to evaluate rice diversity (indica and japonica sub-groups) for partial resistance. The analysis of partial resistance requires the removal of necrotic, HR-like, lesions that could result from defeated R genes triggering attenuated gene-for-gene resistance [32]. To meet this criterion, we selected rice/M. oryzae interactions that were as close as possible to compatibility. Based on preliminary results (J L Nottéghem, personal communication), we selected 23 rice cultivars. We also included five rice accessions that are commonly used in the research community and for which genomic and/or genetic information exists (IR64, Nipponbare, Azucena, Maratelli and Sariceltik). These cultivars represent 57% of overall rice allelic diversity, 51% for japonica sub-group and 55% for the indica sub-group as estimated by allelic diversity of microsatellites markers (Garris et al, 2005). These 28 rice accessions were inoculated with four multivirulent isolates with broad-spectrum virulence (see Methods and FIG. 15), and partial resistance was estimated. An index was created for partial resistance that measures fungal growth in planta as quantified by Q-PCR (see Methods and FIG. 15). In calculating the partial resistance index, we were careful to remove as much as possible background gene-for-gene interactions. These were manifested by extremely low quantities of fungal growth and/or HR-like lesions. Out of 25 rice accessions tested, 23 were finally selected as representing most of partial resistance quantitative diversity. The genotypes showing high resistance against all M. oryzae strains (CT13432 and NPE826; FIG. 1 and Additional File 1) were removed from the analysis as they likely reflect complete resistance driven by major R-genes. Thus, a total of 23 rice accessions were characterized for partial resistance to rice blast disease and bacterial blight (FIG. 1).

From this analysis, it appears that rice accessions from the tropical japonica sub-group were over-represented among accessions with elevated levels of partial resistance to rice blast (FIGS. 1 and 15). Partial resistance index ranged from 30 (tropical japonica Moroberekan) to 1.3 (indica Padi Boenor). Thus partial resistance to blast fungus is highly variable across rice diversity and can vary up to 23-fold. There was no obvious correlation between partial resistance to blast and bacterial blight.

C. Constitutive Expression of Defense as a Better Indicator of Partial Resistance than Inducible Expression We first addressed the question of the relative roles of inducible and constitutive expression of selected defense-related genes in partial resistance. For this purpose, we designed an experiment with a limited number of marker genes (11) and six representative rice accessions. This experiment was repeated three times independently to monitor gene expression before infection and 1, 2, 3 and 4 days post-inoculation (dpi).

Figure 2:
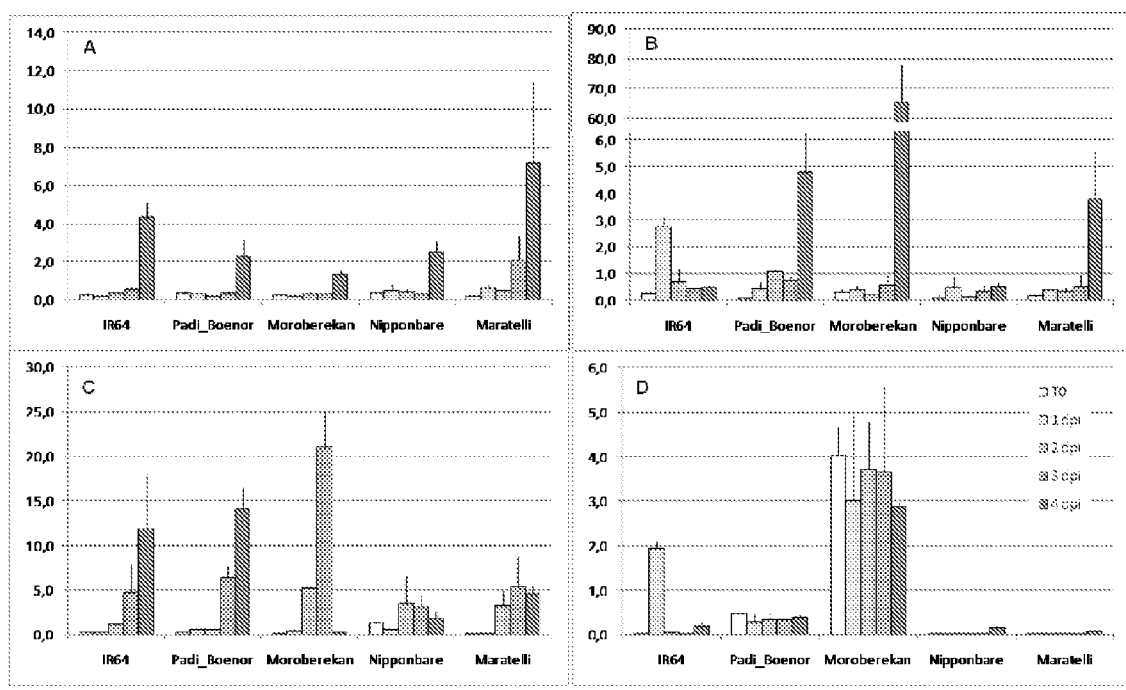
Figure 3:
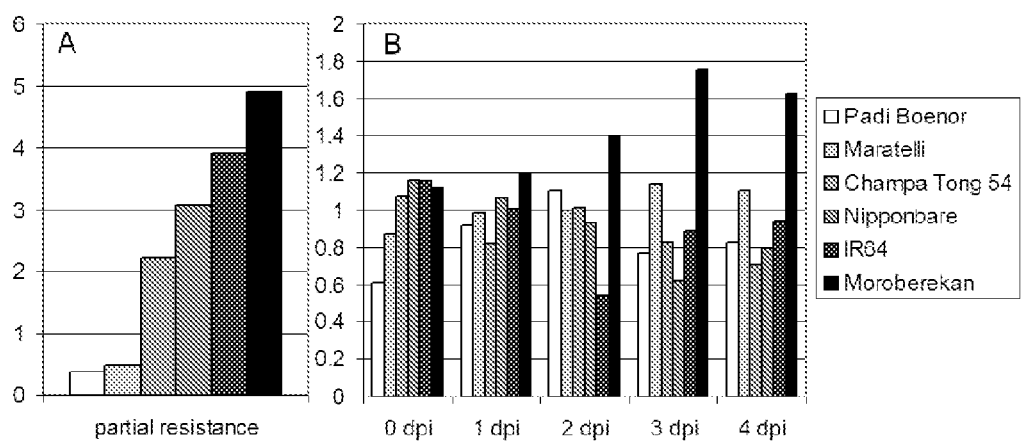

This experiment indicated that most of the defense-related genes selected were induced after infection (FIGS. 2 and 16). In order to compare partial resistance to gene expression, we built an expression index that takes into account the expression values of all genes (See Methods and FIG. 18). We could then compare the partial resistance index to the expression indexes at the different times before and after infection (FIG. 3).

Regression analysis (FIG. 19) suggests that there is a good correlation between both indexes before infection ($R^2=0.8$, $p<0.0027$) but no statistically significant correlation of these indexes after infection. Thus the data on expression of this selected marker genes evaluated on this small set of rice cultivars suggests that expression before infection, more than after infection, correlates with partial resistance.

D. The Level of Constitutive Expression of Defense-Related Genes is Highly Polymorphic Across Rice Diversity We wanted to further extend this analysis to a larger set of rice genes and accessions. We measured constitutive gene expression of 21 genes representative of the rice defense arsenal (FIG. 16) in the 23 rice accessions for which we measured partial resistance. Constitutive expression was measured in seven independent experiments at the time when inoculation is usually performed and when partial resistance has started to develop (3 weeks after sowing).

When treated individually, the constitutive expression of each gene revealed several points. First, we observed an important variability of the expression levels across cultivars. For example, the expression level of the classical defense gene PBZ1 vary up to 35-fold, with a value of 0.02 in one of the most susceptible cultivar, Sariceltik, and a value of 0.7 in the most resistant cultivar, Moroberekan. Second, the pattern of constitutive expression was sometimes different between the indica and japonica rice sub-groups (e.g. the BURP gene).

Figure 4:
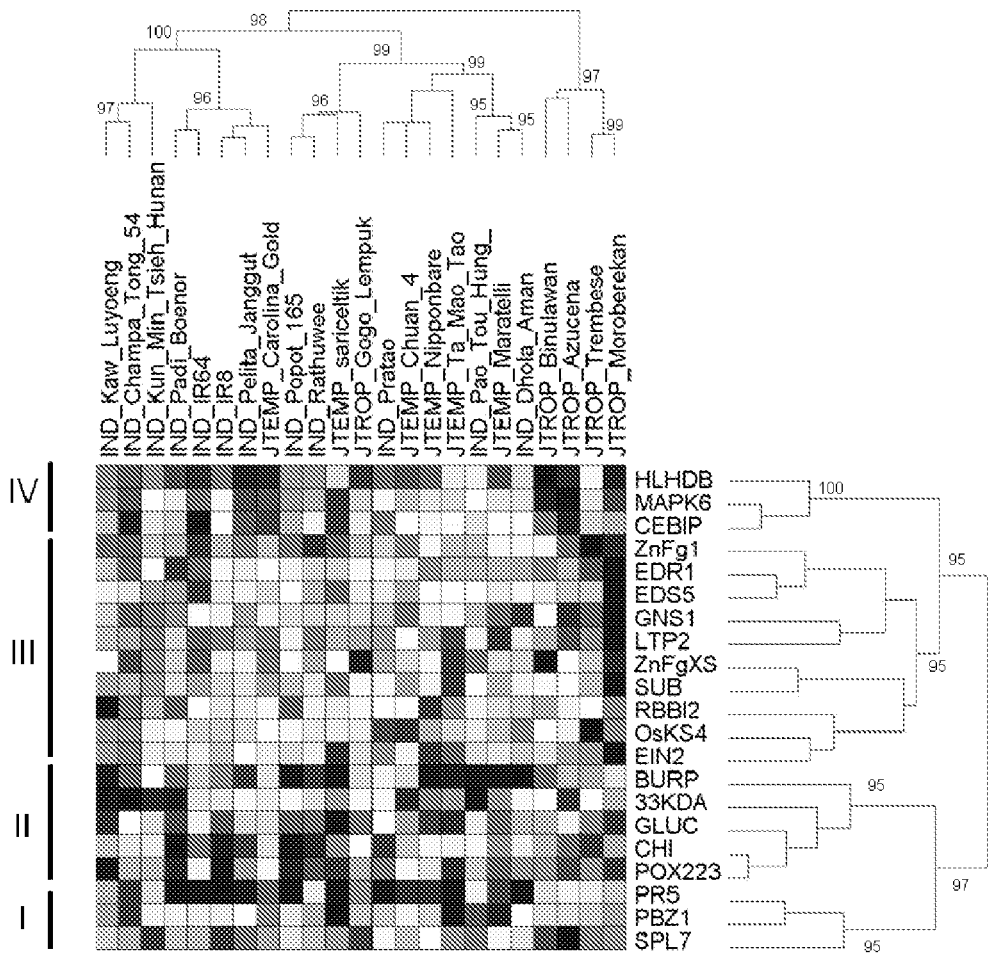

We used hierarchical clustering to identify groups of genes that were co-regulated across rice diversity (FIG. 4). Several groups of genes that are co-regulated were found, as supported by bootstrap analysis. The first group (regulon I) contains both PR genes and regulatory genes (PBZ1, PR5 and SPL7). The second group (regulon II) mostly contains PR genes (BURP, 33 kDa, GLUC, POX223 and CHI). The third group (regulon III) consists in a last large group of genes that contains both regulatory and PR genes. The last group (regulon IV) contains genes involved in recognition (CEBiP) and signal transduction (MAPK6, HLHDB).

Hierarchical clustering of the data also confirmed that the genetic background considerably affects constitutive expression of the selected genes (FIG. 4). For instance, the sub-group of tropical japonica rice appeared clearly different from the other genetic groups of rice. This difference is mostly due to genes from regulons I and II. Thus, rice cultivars from different sub-groups display contrasting capacities to express defense-related genes before infection, suggesting contrasting regulation capacities.

E. The Level of Constitutive Expression of Defense-Related Genes Strongly Correlates with Partial Resistance Across Rice Diversity It was noteworthy from previous observations that the tropical japonica subgroup is also the genetic sub-group displaying the highest partial resistance index in our analyses (FIG. 1). In order to search for global correlations between constitutive expression of tested genes and the measured partial resistance index, the expression data of the 21 selected defense-related genes in the 23 rice genotypes was analyzed using the expression index already used (See Methods and FIG. 18). We found a strong correlation between constitutive expression of defense-related genes and partial resistance ($R^2=0.83$, $p<1.756e-6$; FIG. 5). Thus, the previous observation on a small subset of rice diversity (FIGS. 3 and 19) holds true when tested on a sample of cultivars representing a large subset of rice diversity. Similar results were also found when separately testing indica and japonica sub-groups.

Using Principal Component Analysis and ANOVA (FIG. 20), we could identify the genes that, in our selection, were the most significantly reflecting the correlation between constitutive expression of defense and partial resistance. The PBZ1 gene from regulon I was found to be the best marker of constitutive expression of defense-related genes across indica and japonica rice sub-groups. Thus, for the PBZ1 gene, the observed correlation between constitutive expression and partial resistance holds true for almost all the 23 rice genotypes tested, despite the diversity explored. Another gene from regulon I, the SPL7 gene, appeared to be a good marker for indica genotypes. The BURP and GLUC genes from regulon II were good markers for the japonica sub-group. Overall, this analysis across rice diversity suggests that constitutive expression of defense-related genes and partial resistance are highly correlated.

F. Constitutive Expression of Defense Systems is Developmentally Controlled

Partial resistance is well known to increase along plant development [19]. In particular, in rice there is a strong difference between resistance to blast in a 2-weeks old plant (juvenile—susceptible) and resistance in a 3-week old plant (young adult—resistant). It is also quite common that the last emerged leaf (leaf n) is often more susceptible than the leaf that emerged one week before (leaf n–1). We thus tested whether constitutive expression of defense-related genes was following the same developmental patterns. We chose the tropical japonica cultivars Moroberekan and Azucena, as they are good representative of constitutive expression of defense-related genes (FIG. 4). Constitutive expression of defense-related genes was measured in plants aged from 2 to 8 weeks, on two different leaves (last and before the last leaf emerged). As shown in FIG. 6, the expression of these defense-related genes followed the same developmental pattern than partial resistance with a strong increase in expression between two and three weeks after sowing. This was true for the eight marker genes tested (data not shown). This increase of expression was maintained for half of the genes tested. We have yet no explanation for the decrease of expression of some genes like RBBI2 later in development. We also observed that constitutive expression of defense-related genes was overall higher in leaf n–1 than in leaf n, a pattern very similar to age-related partial resistance. Thus, this striking parallel between partial resistance and expression of defense-related genes during plant development further supports our hypothesis that partial resistance can be explained by constitutive expression of defense-related genes.

G. Constitutive Level of SA and Ethylene do not Explain Partial Resistance

There is a previous report that salicylic acid (SA) a signaling molecule involved in disease resistance could play a role in partial resistance of rice to *M. oryzae* [33]. Jasmonic acid (JA) [34] and ethylene [35] are also identified as important signaling molecules in plant disease resistance. We asked whether these signaling molecules could relate to constitutive expression of defense-related genes. We evaluated the SA and ethylene pathways by direct quantification of SA and ethylene. We monitored the implication of the JA pathway by using the marker gene RCI1 [36].

The constitutive expression of RCI1 did not correlate with partial resistance to *M. oryzae* (FIG. 20). Thus the JA constitutive levels, as monitored by the RCI1 gene, do not seem to contribute to partial resistance.

SA and ethylene were directly extracted and quantified. The amount of these two molecules was very different across rice diversity (FIG. 7). In each rice sub-group, the constitutive quantities of SA or ethylene were similar in rice accessions showing elevated and weak partial resistance (FIGS. 7A and 7C). We could not detect any correlation between the level of partial resistance and the levels of SA or ethylene (data not shown). However, we observed that constitutive amounts of SA are 2-fold higher in indica cultivars than in japonica cultivars and this difference is statistically significant (FIG. 7B). Conversely, the constitutive levels of ethylene were higher in japonica than in indica cultivars (FIG. 7D). Thus, SA and ethylene constitutive levels negatively correlate ($R^2=-0.81$, $P<5.2\times10^{-6}$). Although we detected a high level of polymorphism for SA and ethylene in rice, we could not find any correlation between these molecules and partial resistance, nor with constitutive expression of defense-related genes.

H. Co-Localization of QTLs Controlling Constitutive Expression of Defense-Related Genes and QTLs for Partial Resistance A prediction of our hypothesis is that we should be able to find areas of the rice genome that control both constitutive expression of defense-related genes and partial resistance. In order to identify such regions, we initiated a QTL analysis on gene expression. Expression data has been recently used as quantitative traits for QTL analysis [37]. The resulting QTLs are called eQTLs, for expression QTLs. Two types of eQTLs are expected: cis-eQTLs that are located at the same locus that the gene monitored for expression (structural gene) and trans-eQTLs that are located at another locus.

We used two japonica X indica mapping populations: the Moroberekan X CO39 population with 60 recombinant inbred lines (RILs) [38] and the Azucena X IR64 population with 84 RILs [39]. Among the genes tested in this study (FIG. 16), we looked for genes that would show the strongest constitutive expression polymorphism between the parents of the available RIL populations (data not shown). The BURP and CHI genes showed the strongest polymorphism and were chosen for eQTL analysis. For each mapping population, two to three independent experiments were done in which constitutive expression of these genes was monitored as well as disease symptoms and used as quantitative traits.

The FIG. 8 shows the eQTL and QTL detected with LOD>3 (FIG. 22) in at least two independent experiments (false discovery rate of 0.001). Three eQTLs (chromosome 1, 7 and 11) for the BURP gene and three eQTLs for the CHI gene (two on chromosome 7 and one on chromosome 11) were found. Most of them were trans eQTLs. One cis-eQTL was detected for the CHI gene. Quite remarkably, two eQTLs were common to the CHI and the BURP genes, suggesting that the constitutive expression of these genes could be controlled by the same locus. The eQTLs for BURP and CHI found on chromosomes 1 and 7 respectively were observed in both mapping populations, further supporting the existence of eQTLs in these regions. In all cases the favorable allele increasing constitutive expression was from the tropical japonica parental line (Moroberekan and Azucena). For the BURP gene, this is consistent with the observed positive correlation between constitutive expression of this gene and partial resistance in japonica but not indica sub-group (FIG. 20).

Twelve QTLs for blast partial resistance were found (FIG. 22). It was striking that two of these QTLs, one on chromosome 7 (RG4 marker) and one on chromosome 11 (RG103A marker) are co-localizing with eQTL. This is the first genetic evidence that the control of constitutive expression of a defense-related genes could account for partial resistance.

I. P33 KD Expression Variation in Wheat after Pathogen Infection

Global analysis of the variation of gene expression was performed during *Septoria tritici* infection. In the following experiment, p33 KD was identified as a candidate gene for plant response to pathogens infection. Two genotypes, Cadenza and Veranopolis, harboring different Stb resistance genes are used. For both genotypes, control and *Septoria tritici* specific type infected plantlets are analysed. RNAs from plantlets leaf are extracted and different biological replicates are analysed with GeneChip Wheat Genome Array (Affimetrix). P33 KD expression profile is obtained with 3 Affymetrix probes: Ta.25531.1.A1_at, Ta.25531.2.A1_at et Ta.25531.2.A1_x_at.

The transcriptomic data are presented FIGS. 9 and 10. They show that p33 KD is over-expressed from two days after infection (dai) compared to the control.

J. Overexpression of p33 Kd or BURP in Wheat Plants

Transformation Constructs for p33 KD or BURP Over-Expression

SapI-digested DNA fragments encoding the Rice ubiquitin 3 promoter, the synthetic gene SynOs33 kD TaMod encoding p33 KD (SEQ ID NO: 3) and the terminator AtSac66 were ligated into the Sap 1 site of the binary plasmid pBIOS2028 forming the new plasmid pBIOS2196 (FIG. 11). pBIOS2028 is derived from plasmid pSCV1, and comprises the gene encoding for NPTII under the control of subterranean clover virus SCv4 promoter.

Wheat Transformation Protocol

Wheat transformation was performed on NB1 spring wheat variety using an *Agrobacterium tumefaciens* strain containing the pBIOS2196 plasmid. Regenerated transgenic plants have been selected that contain a single insertion locus and an untruncated T-DNA from pBIOS2196. Wheat transformants are grown and analyzed in greenhouse for pathogens resistance.

The method is essentially similar to the one described in International Application WO 00/63398. Wheat tillers, approximately 14 days post-anthesis (embryos approximately 1 mm in length), are harvested from glasshouse grown plants to include 50 cm tiller stem (22/15° C. day/night temperature, with supplemented light to give a 16 hour day). All leaves are then removed except the flag leaf and the flag leaf is cleaned to remove contaminating fungal spores. The glumes of each spikelet and the lemma from the first two florets are then carefully removed to expose the immature seeds. Only these two seeds in each spikelet are generally uncovered. This procedure is carried out along the entire length of the inflorescence. The ears are then sprayed with 70% IMS as a brief surface sterilization.

*Agrobacterium tumefaciens* strains containing the vector for transformation are grown on solidified YEP media with 20 mg/l kanamycin sulphate at 27° C. for 2 days. Bacteria are then collected and re-suspended in TSIM1 (MS media with 100 mg/l myo-inositol, 10 g/l glucose, 50 mg/l MES buffer pH5.5) containing 400 µM acetosyringone to an optical density of 2.4 at 650 nm.

*Agrobacterium* suspension (1 µl) is inoculated into the immature seed approximately at the position of the scutellum: endosperm interface, using a 100 Hamilton, so that all exposed seed are inoculated. Tillers are then placed in water, covered with a translucent plastic bag to prevent seed dehydration, and placed in a lit incubator for 3 days at 23° C., 16 hr day, 45 µEm-2s−1 PAR.

After 3 days of co-cultivation, inoculated immature seeds are removed and surface sterilized (30 seconds in 70% ethanol, then 20 minutes in 20% Domestos, followed by thorough washing in sterile distilled water). Immature embryos are aseptically isolated and placed on W4 medium (MS with 20 g/l sucrose, 2 mg/l 2,4-D, 500 mg/l Glutamine, 100 mg/l Casein hydrolysate, 150 mg/l Timentin, pH5.8, solidified with 6 g/l agarose) and with the scutellum uppermost. Cultures are placed at 25° C. in the light (16 hour day). After 12 days cultivation on W4, embryogenic calli are transferred to W425G media (W4 with 25 mg/l Geneticin (G418)). Calli are maintained on this media for 2 weeks and then each callus is divided into 2 mm pieces and re-plated onto W425G.

After a further 2 week culture, all tissues are assessed for development of embryogenic callus: any callus showing signs of continued development after 4 weeks on selection is transferred to regeneration media MRM 2K 25G (MS with 20 g/l sucrose, 2 mg/l Kinetin, 25 mg/l Geneticin (G418), pH5.8, solidified with 6 g/l agarose). Shoots are regenerated within 4 weeks on this media and then transferred to MS20 (MS with 20 g/l sucrose, pH5.8, solidified with 7 g/l agar) for shoot elongation and rooting.

The presence of the T-DNA, and the number of copies are quantified by Quantitative PCR (qPCR).

Recombinant wheat plants containing a vector expressing p33 kD are grown and analyzed for pathogens resistance.

K. Overexpression of p33 Kd or BURP in Rice

Recombinant rice plants overexpressing p33 Kd were generated following a process similar to that described in Example J.

SEQ ID NO: 1 encoding protein p33 Kd was cloned into plasmid pUbi to generate pUbi::33 kDa (see FIG. 12).

Transgenic plants (Nipponbare background) containing overexpression vector pUbi::33 kDa were compared to transgenic plants containing the empty vector after inoculation with *Magnaporthe oryzae* isolate GY11 which is moderately virulent on Nipponbare. The number of plants showing either resistance (no symptoms), partial resistance (few lesions but no sporulation) and susceptibility (sporulating lesions) was counted. The results are shown FIG. 13. They show that the 33 kDa population is significantly different from the empty vector population (P<0.03). Data from 35 plants tested (overexpressor for 33 kDa-blue bars) and 26 control plants for empty vector (no over-expression of 33 kDa-red bars) expressed as a percent.

Transgenic plants (Nipponbare background) containing overexpression vector pUbi::33 kDa were also compared to transgenic plants containing the empty vector after inoculation with *Magnaporthe oryzae* isolate FR13, which is virulent on Nipponbare. The number of plants showing either resistance (no symptoms), partial resistance (few lesions but no sporulation) and susceptibility (sporulating lesions) was counted. The results are shown FIG. 14. They show that the 33 kDa population is significantly different from the empty vector population (P<0.07). Data from 29 plants tested (over-expressor for 33 kDa-blue bars) and 32 control plants for empty vector (no over-expression of 33 kDa-red bars) expressed as a percent.

L. Discussion

The Expression of Defense-Related Genes and Molecules is Highly Polymorphic in Rice We decided to use rice diversity in order to establish a role of constitutive expression of defense-related genes in partial resistance. We analyzed 23 rice cultivars that were randomly selected in the two major groups of indica and japonica. These cultivars represent up to 57% of rice diversity and thus can be considered as a representative sample. In order to evaluate partial resistance for *Magnaporthe oryzae*, we generated an index that mostly takes into account fungal growth. Complete resistance driven by specific gene-for-gene interactions was removed. Overall, our quantitative index correlates with other measurements of partial resistance like lesion number (XG and JBM, data not shown).

Partial resistance to blast fungus did not correlate with quantitative resistance to rice blight (FIG. 1). This may be due to different lifestyles of the fungal pathogen (hemibiotrophic, growing in the mesophyl) and bacterial pathogen (biotrophic, growing in the xylem) tested. This may also be due to the fact that partial resistance to blast was evaluated on 3-weeks old plants whereas resistance to bacterial blight was evaluated on 8-weeks old plants.

The genes that were used to measure constitutive expression are representative of the disease resistance pathway. Most of the regulators have been demonstrated to be positive regulators of resistance by mutant analysis (See references in FIG. 16). Many of the defense genes studied have also been shown to increase resistance in plants that are over-expressing them [25]. Finally, the OsKS4 gene was selected as a representative gene for the momilactone biosynthetic pathway, one of the major rice phytoalexin [40].

It was clear from our analysis that constitutive expression of the defense-related genes selected was highly polymorphic across rice diversity (FIG. 2). This analysis revealed that the tropical japonica sub-group displays a unique capacity to express defense-related genes before infection (FIG. 4). This observation likely reflects that these genotypes possess polymorphic and/or unique regulators of disease resistance.

The constitutive amounts of signaling molecules like salicylic acid and ethylene is also extremely polymorphic (FIG. 7), especially between indica and japonica cultivars. Comparing this polymorphism to expression polymorphism of other plant metabolic pathways would tell us whether these ELP (expression level polymorphism) are comparable or not. An analysis in *Arabidopsis* suggests that defense-related genes display elevated ELPs as compared to genes belonging to other pathways [29]. It is also noteworthy that sequence polymorphism of defense-related genes is low in *Arabidopsis* [42]. It is thus likely that disease resistance polymorphism results more from expression than from polymorphism at the protein level, with the exception of gene-for-gene polymorphism.

Preformed Defense, but not Induced Defense, is a Hallmark of Partial Resistance to the Rice Blast Fungus Our hypothesis was that the constitutive expression of defense-related genes was contributing to partial resistance. This was initially based on observation on a few rice cultivars and genes (EV and JBM, data not shown). This was also motivated by several piece of literature reporting that physical barriers [20, 22] and preformed antimicrobial molecules [23] play an important role in disease resistance. We thus addressed the question of a putative contribution of defense-related genes in general in partial resistance. We built an index of gene expression where all genes participate to the same extent to the final value (See Methods and FIG. 18). When compared to the index of partial resistance, we found a very strong correlation between constitutive expression of defense-related genes and partial resistance (FIG. 5). This correlation was extremely robust as we observed it in seven independent experiments in the past two years. We conclude that this constitutive expression of defense-related genes is a preformed defense system that contributes to partial resistance.

The group of tropical japonica cultivars showed an atypical pattern of constitutive expression of defense-related genes (FIG. 4). These cultivars also displayed a high index of partial resistance and of constitutive expression of defense. This observation suggests that this rice sub-group harbors a particular preformed defense system.

Some genes like the regulatory gene SPL7 and the PR gene PBZ1 were good markers of preformed defense (FIG. 20). The only PRR gene tested here, the CeBiP gene, was not a good marker of preformed defense. Cloned R genes [18] and more recently identified receptor-like genes (WAKI) [43] need to be tested to determine if constitutive expression of defense-related genes involves all steps of the basal and gene-for-gene resistance pathways. Finding more genes with an expression pattern correlated to partial resistance will help us to build gene sets to further studying preformed defense.

There was no obvious correlation between partial resistance and expression after infection of the defense-related genes tested (FIGS. 3 and 19). Since the infection process of rice by *M. oryzae* occurs very early after inoculation, it is possible that we underscored early time points (less than 24 h after infection). It remains possible that gene expression in the very early steps of infection also correlate with partial resistance. It is also extremely difficult to estimate the part of partial resistance that can be attributed to preformed and induced defense. Identifying genes that control preformed but not induced defense could help defining the respective contribution of each system. Without rejecting the probable contribution of induced defense in partial resistance, our results strongly suggest that constitutive expression of defense-related genes highly contributes to partial resistance.

Preformed Defense Parallels the Developmental Control of Partial Resistance

One of the best evidence for a contribution of preformed defense to partial resistance comes from the observation that these two phenomena are coordinated during development. Partial resistance is well known in rice to be developmentally regulated [19]. When we measured constitutive expression of defense-related genes, we observed that this expression was following the increase of partial resistance during plant growth. The constitutive expression of all genes tested dramatically increase between juvenile (2-week old plant) and young adult plants (3-week old plants) (FIG. 6). Such a massive effect suggests that there is a major control of development on the expression of preformed defense. Recently, Zhao et al [45] also observed that the constitutive expression of the R genes Xa3/Xa26 and Xa21 were developmentally controlled. This could easily explain in this case why gene-for-gene resistance driven by these genes was effective in adult plants but not in juvenile plants. Finding common regulatory points between development and defense may help us understanding how partial resistance is developmentally controlled.

The Regulation of Preformed Defense has Yet to be Identified

In order to get further insights on the way preformed defense is deployed by rice, we tested the implication of three signaling pathways controlled by salicylic acid, jasmonic acid and ethylene in constitutive expression of defense-related genes. We did not find evidence that these pathways were involved. This was unexpected for the SA pathway since previous report [33] suggested that constitutive SA levels were correlated to M. oryzae resistance. When we closely examined this report, we found out that the disease index used by Silverman and colleagues was not defined and that disease resistance in their case most likely correlated with indica/japonica differences. This could simply reflect the fact that some M. oryzae isolates are better adapted on one rice subgroup than on another. We circumvented this difficulty by trying to incorporate in our disease index only partial resistance as monitored by using multivirulent isolates of M. oryzae. We conclude that neither constitutive expression of SA, JA nor ethylene pathway correlates with ELP of defense-related genes.

Alternatively, preformed defense could result from the leakage of the disease resistance pathways. For example, assuming that some signaling is constantly triggered by the environment, rice cultivars having efficient but leaky regulatory pathways would also display elevated levels of defense-related genes in the absence of infection. This mechanism would require positive regulators of disease resistance to be very active and negative regulators to be quite inactive. This mechanism would be similar to the mechanism by which the barley mlo gene confers resistance to powdery mildew. The MLO gene is a negative regulator of disease resistance and recessive alleles (mlo) of this gene confer broad-spectrum resistance [46]. Some mlo alleles are weak negative regulators such that the plant constitutively expresses parts of the disease resistance pathway, leading to spontaneous cell-death that resembles HR [47].

Forward genetics is one way to identify the genes that regulate preformed defense. Using QTL mapping, we show that preformed defense is amenable for genetics. Several regions of the rice genome controlling preformed expression of the CHI and BURP genes were identified (FIG. 8). The architecture of this control is probably complex since our analysis of only two genes revealed six eQTLs. However, the observation that the BURP and CHI belong to the same regulon (FIG. 4) is consistent with the observation that two eQTLs are common to these genes (FIG. 8). These regions of chromosome 7 and 11 may contain regulators of preformed defense that are specific to the tropical japonica sub-groups. Fine mapping of these regions will help us identify the genes that control preformed defense and partial resistance.

More importantly, we show the first genetic evidence that two eQTLs controlling constitutive expression of the CHI and BURP genes co-localize with two QTLs for partial resistance. Given the number of genetic markers used for mapping (133), the number of QTL (11) and eQTL (6) found, the probability to find such co-localizations was very low (P=0.011). A more detailed analysis will be necessary to establish a functional relationship between these two phenomena.

Interestingly, one of the eQTL controlling CHI constitutive expression co-localizes with the CHI structural gene on chromosome 7. Thus this eQTL could be a cis-eQTL. We did not find a potential cis-eQTL for the BURP gene, suggesting that constitutive expression for this gene is mostly controlled in trans. Given the yet imprecise position of the eQTLs, the eQTL controlling the CHI around the RG4 marker could also be a trans eQTL. In such a case, this region around RG4 marker on chromosome 7 could be a common regulator of constitutive expression for BURP and CHI.

Our QTL analysis already pinpoints some regulatory candidates that co-localize (4 Mb range) with several eQTLs. The eQTL on chromosome 1 co-localizes with OsWRKY13 [49]. This transcription factor has been shown to be involved in blast disease resistance as plants over-expressing OsWRKY13 show enhanced resistance to this pathogen. Plants over-expressing OsWRKY13 also displayed constitutive, elevated, levels of expression of defense-related genes but PBZ1 was down-regulated. Thus this gene is unlikely a good candidate for regulating preformed defense. The eQTL on chromosome 7 (close to the RG4 marker) co-localizes with the OsDR8 [41] and the CIGR1 [48] genes. Preliminary analysis of the cigr1 mutant suggests that this gene is not responsible for the eQTL (Blein M, XG and JBM, data not shown). The OsDR8 gene is involved in the vitamin B1 biosynthesis pathway and in thiamine accumulation [41] is also found within 4 Mb of the RG4 marker on chromosome 7. Interestingly, plants silenced for OsDR8 show increased susceptibility to M. oryzae and reduced accumulation, before infection (as well as after infection) of several PR genes, including POX223 but not PBZ1. This is only partly consistent with a possible role of OsDR8 in preformed of defense. Consistent with the implication of the thiamine pathway in preformed defense, thiamine is known to be an inducer of defenses in plants, including rice [44]. Finally, the eQTL close to marker RG351 on chromosome 7 co-localizes with the rTGA2.1 gene [55]. Although silencing of the rTGA2.1 gene increased the constitutive expression of defense-related genes, it is yet unknown whether this mutation affects resistance to M. oryzae. Such attempt to co-localize known regulatory genes with eQTL is overall risky and fine mapping will be required to identify the genes explaining these eQTLs.

Preformed Defense Systems as a Way to Respond to Environmental Stresses in Plants Plants have evolved sophisticated inducible systems to respond to pathogen challenge [1]. Expression level polymorphism (ELP) has been shown to be important for the gene-for-gene resistance pathway [e.g. 30, 31] but there was up to now no indication that ELP could play a role in partial resistance. By looking at ELP in partial resistance of rice to M. oryzae, we provide several lines of evidence that constitutive expression of defense-related genes correlates with partial resistance in naturally occurring diversity. This is the first evidence of the role of constitutive expression of defense-related genes in disease resistance. Plants have deployed such a proactive strategy to face abiotic stresses [50, 51]. For example, a large portion of the genes that are normally induced by zinc stress in Arabidopsis thaliana are constitutively highly expressed in A. halleri, a species of the Arabidopsis genus showing enhanced tolerance to zinc. Thus, constitutive expression of zinc-responsive genes has been proposed as a mechanism by which A. halleri naturally increases its tolerance to zinc [50]. Using a similar approach, Taji et al [51] showed that a large number of abiotic or biotic stress-inducible Arabidopsis thaliana genes were expressed under normal growth conditions in salt cress (Thellungiella halophila), a naturally salt tolerant plant species. Thus plants seem to have evolved proactive, non-inducible systems to face abiotic stresses.

Therefore, it appears that constitutive expression of the adapted repertoire of genes is a general strategy used by plants to face environmental pressure. This is consistent with our current knowledge on trait evolution which poses that regulatory polymorphism might better account for phenotypical variability than structural polymorphism [52].

CONCLUSIONS

Past research has largely focused on inducible mechanisms to explain disease resistance. We provide three lines of evidence that constitutive expression of defense-related genes significantly contributes to partial resistance. The role of preformed defense is supported by our diversity analysis, our analysis of the phenomenon during development and genetic evidence. Besides the fundamental aspect of this finding, this invention also has important consequences for the breeding strategies. Although indica and japonica sub-groups show some differences in their ability to express preformed defense, this study shows that constitutive expression of defense-related genes is a good prediction tool for identifying rice accessions with elevated partial resistance, a form of durable resistance.

REFERENCES

1. Jones J D, Dangl J L: The plant immune system. *Nature* 2006, 444(7117):323-329
2. Bent A F, Mackey D: Elicitors, effectors, and R genes: the new paradigm and a lifetime supply of questions. *Annu Rev Phytopathol* 2007, 45:399-436
3. Kaku H, Nishizawa Y, Ishii-Minami N, Akimoto-Tomiyama C, Dohmae N, Takio K, Minami E, Shibuya N: Plant cells recognize chitin fragments for defense signaling through a plasmamembrane receptor. *Proc Natl Acad Sci USA* 2006, 103(29):11086-91
4. Mishra N S, Tuteja R, Tuteja N: Signaling through MAP kinase networks in plants. *Arch Biochem Biophys* 2006, 452(1):55-68
5. Eulgem T, Somssich I E: Networks of WRKY transcription factors in defense signaling. *Curr Opin Plant Biol* 2007, 10(4):366-71
6. Chern M S, Fitzgerald H A, Yadav R C, Canlas P E, Dong X, Ronald P C: Evidence for a disease-resistance pathway in rice similar to the NPR1-mediated signaling pathway in *Arabidopsis*. *Plant J* 2001, 27(2): 101-13
7. Fitzgerald H A, Chern M S, Navarre R, Ronald P C: Overexpression of (At)NPR1 in rice leads to a BTH- and environment-induced lesion-mimic/cell death phenotype. *Mol Plant Microbe Interact* 2004, 17(2):140-51
8. Chern M, Fitzgerald H A, Canlas P E, Navarre D A, Ronald P C: Overexpression of a rice NPR1 homolog leads to constitutive activation of defense response and hypersensitivity to light. *Mol Plant Microbe Interact* 2005, 18(6): 511-20
9. Makandar R, Essig J S, Schapaugh M A, Trick H N, Shah J: Genetically engineered resistance to *Fusarium* head blight in wheat by expression of *Arabidopsis* NPR1. *Mol Plant Microbe Interact* 2006, 19(2):123-9
10. Yuan Y, Zhong S, Li Q, Zhu Z, Lou Y, Wang L, Wang J, Wang M, Li Q, Yang D, HeZ: Functional analysis of rice NPR1-like genes reveals that OsNPR1/NH1 is the rice orthologue conferring disease resistance with enhanced herbivore susceptibility. *Plant Biotechnol J* 2007, 5(2): 313-24
11. Vergne E, Ballini E, Marques S, Sidi Mammar B, Droc G, Gaillard S, Bourot S, DeRose R, Tharreau D, Nottéghem J L, Lebrun M H, Morel J B: Early and specific gene expression triggered by rice resistance gene Pi33 in response to infection by ACE1 avirulent blast fungus. *New Phytol* 2007, 174(1):159-71
12. Vergne E, Ballini E, Droc G, Tharreau D, Nottéghem J L, Morel J B: ARCHIPELAGO: a dedicated resource for exploiting past, present, and future genomic data on disease resistance regulation in rice. *Mol Plant Microbe Interact* 2008, 21(7):869-78
13. Peters R J: Uncovering the complex metabolic network underlying diterpenoid phytoalexin biosynthesis in rice and other cereal crop plants. *Phytochemistry* 2006, 67(21): 2307-17
14. Jwa N S, Agrawal G K, Tamogami S, Yonekura M, Han O, Iwahashi H, Rakwal R: Role of defense/stress-related marker genes, proteins and secondary metabolites in defining rice self-defense mechanisms. *Plant Physiol Biochem* 2006, 44 (5-6):261-73
15. Van Loon L C, Rep M, Pieterse C M: Significance of inducible defense-related proteins in infected plants. *Annu Rev Phytopathol* 2006, 44:135-62
16. Hückelhoven R. Cell wall-associated mechanisms of disease resistance and susceptibility. *Annu Rev Phytopathol* 2007, 45:101-27
17. Greenberg J T, Yao N: The role and regulation of programmed cell death in plant-pathogen interactions. *Cell Microbiol* 2004, 6(3):201-11
18. Ballini E, Morel J B, Droc G, Price A, Courtois B, Nottéghem J L, Tharreau D: A genome-wide meta-analysis of rice blast resistance genes and quantitative trait loci provides new insights into partial and complete resistance. *Mol Plant Microbe Interact* 2008, 21(7):859-68
19. Develey-Rivière M P, Galiana E: Resistance to pathogens and host developmental stage: a multifaceted relationship within the plant kingdom. *New Phytol* 2007, 175(3):405-16.
20. Skamnioti P, Gurr S J: *Magnaporthe grisea* Cutinase2 Mediates Appressorium Differentiation and Host Penetration and Is Required for Full Virulence. *Plant Cell* 2007, 19(8):2674-89
21. Juge N: Plant protein inhibitors of cell wall degrading enzymes. *Trends Plant Sci* 2006, 11(7):359-67
22. Ma J F, Yamaji N: Silicon uptake and accumulation in higher plants. *Trends Plant Sci* 2006, 11(8):392-7
23. Morrissey J P, Osbourn A E: Fungal resistance to plant antibiotics as a mechanism of pathogenesis. *Microbiol Mol Biol Rev* 1999, 63(3):708-24
24. Hammond-Kosack K E, Parker J E: Deciphering plant-pathogen communication: fresh perspectives for molecular resistance breeding. *Curr Opin Biotechnol* 2003, 14(2): 177-93
25. Deltail A, Zhang J, Lessard P, Morel J B: Transgenic approaches for improving rice disease resistance: 2009 status. *Rice, in press*.
26. Noutoshi Y, Ito T, Seki M, Nakashita H, Yoshida S, Marco Y, Shirasu K, Shinozaki K: A single amino acid insertion in the WRKY domain of the *Arabidopsis* TIR-NBS-LRR-WRKY-type disease resistance protein SLH1 (sensitive to low humidity 1) causes activation of defense responses and hypersensitive cell death. *Plant J* 2005, 43(6):873-88
27. Petersen M, Brodersen P, Naested H, Andreasson E, Lindhart U, Johansen B, Nielsen H B, Lacy M, Austin M J, Parker J E, Sharma S B, Klessig D F, Martienssen R, Mattsson O, Jensen A B, Mundy J: *Arabidopsis* map kinase 4 negatively regulates systemic acquired resistance. *Cell* 2000, 103(7):1111-20
28. Shimono M, Sugano S, Nakayama A, Jiang C J, Ono K, Toki S, Takatsuji H: Rice WRKY45 plays a crucial role in benzothiadiazole-inducible blast resistance. *Plant Cell* 2007, 19(6):2064-76

29. Kliebenstein D J, West M A, van Leeuwen H, Kim K, Doerge R W, Michelmore R W, St Clair D A: Genomic survey of gene expression diversity in *Arabidopsis thaliana*. *Genetics* 2006, 172(2):1179-89
30. Grant M R, Godiard L, Straube E, Ashfield T, Lewald J, Sattler A, Innes R W, Dangl J L: Structure of the *Arabidopsis* RPM1 gene enabling dual specificity disease resistance. *Science* 1995, 269(5225):843-6
31. Gassmann W, Hinsch M E, Staskawicz B J: The *Arabidopsis* RPS4 bacterial-resistance gene is a member of the TIR-NBS-LRR family of disease-resistance genes. *Plant J* 1999, 20(3):265-77
32. Talukder Z I, Tharreau D, Price A H: Quantitative trait loci analysis suggests that partial resistance to rice blast is mostly determined by race-specific interactions. *New Phytologist* 2004, 162(1):197-209
33. Silverman P, Seskar M, Kanter D, Schweizer P, Metraux J P, Raskin I: Salicylic Acid in Rice (Biosynthesis, Conjugation, and Possible Role). *Plant Physiol* 1995, 108(2): 633-639
34. Agrawal G K, Tamogami S, Han O, Iwahashi H, Rakwal: Rice octadecanoid pathway. *Biochem Biophys Res Commun* 2004, 317(1):1-15.
35. Iwai T, Miyasaka A, Seo S, Ohashi Y: Contribution of ethylene biosynthesis for resistance to blast fungus infection in young rice plants. *Plant Physiol* 2006, 142(3): 1202-15.
36. Schaffrath U, Zabbai F, Dudler R: Characterization of RCI-1, a chloroplastic rice lipoxygenase whose synthesis is induced by chemical plant resistance activators. *Eur J Biochem* 2000, 267(19):5935-42
37. West M A, Kim K, Kliebenstein D J, van Leeuwen H, Michelmore R W, Doerge R W, St Clair D A: Global eQTL mapping reveals the complex genetic architecture of transcript-level variation in *Arabidopsis*. *Genetics* 2007, 175 (3): 1441-50
38. Wang G L, Mackill D J, Bonman J M, McCouch S R, Champoux M C, Nelson R J: RFLP mapping of genes conferring complete and partial resistance to blast in a durably resistant rice cultivar. *Genetics* 1994, 136(4): 1421-34
39. Guiderdoni E, Galinato E, Luistro J, Vergara G: Anther culture of tropical japonica x indica hybrids of rice (*Oryza sativa* L.). *Euphytica* 1992, 62:219-224
40. Shimura K, Okada A, Okada K, Jikumaru Y, Ko K W, Toyomasu T, Sassa T, Hasegawa M, Kodama O, Shibuya N, Koga J, Nojiri H, Yamane H: Identification of a biosynthetic gene cluster in rice for momilactones. *J Biol Chem* 2007, 282(47):34013-8.
41. Wang G, Ding X, Yuan M, Qiu D, Li X, Xu C and Wang S: Dual function of rice OsDR8 gene in disease resistance and thiamine accumulation. *Plant Molecular Biology* 2006, 60:437-449.
42. Bakker E G, Traw M B, Toomajian C, Kreitman M, Bergelson J: Low levels of polymorphism in genes that control the activation of defense response in *Arabidopsis thaliana*. *Genetics* 2008, 178(4):2031-43.
43. Li H, Zhou S Y, Zhao W S, Su S C, Peng Y L: A novel wall-associated receptor-like protein kinase gene, OsWAK1, plays important roles in rice blast disease resistance. *Plant Mol Biol* 2009, 69(3):337-46.
44. Ahn, I.-P., Kim, S. and Lee, Y.-H.2005: Vitamin B1 functions as an activator of plant disease resistance. *Plant Physiol* 2005, 138:1505-1515.
45. Zhao J, Fu J, Li X, Xu C, Wang S: Dissection of the factors affecting development-controlled and race-specific disease resistance conferred by leucine-rich repeat receptor kinase-type R genes in rice. *Theor Appl Genet* 2009, 119 (2):231-9
46. Peterhänsel C, Lahaye T: Be fruitful and multiply: gene amplification inducing pathogen resistance. *Trends Plant Sci* 2005, 10(6):257-60.
47. Wolter M, Hollricher K, Salamini F, Schulze-Lefert P: The mlo resistance alleles to powdery mildew infection in barley trigger a developmentally controlled defense mimic phenotype. *Mol Gen Genet* 1993, 239 (1-2):122-8
48. Day R B, Tanabe S, Koshioka M, Mitsui T, Itoh H, Ueguchi-Tanaka M, Matsuoka M, Kaku H, Shibuya N, Minami E: Two rice GRAS family genes responsive to N-acetylchitooligosaccharide elicitor are induced by phytoactive gibberellins: evidence for cross-talk between elicitor and gibberellin signaling in rice cells. *Plant Mol Biol* 2004, 54(2):26'-72.
49. Qiu D, Xiao J, Ding X, Xiong M, Cai M, Cao Y, Li X, Xu C, Wang S: OsWRKY13 mediates rice disease resistance by regulating defense-related genes in salicylate- and jasmonate-dependent signaling. *Mol Plant Microbe Interact* 2007, 20(5):492-9.
50. Becher M, Talke I N, Krall L, Krämer U: Cross-species microarray transcript profiling reveals high constitutive expression of metal homeostasis genes in shoots of the zinc hyperaccumulator *Arabidopsis halleri*. *Plant J* 2004, 37(2):251-68
51. Taji T, Seki M, Satou M, Sakurai T, Kobayashi M, Ishiyama K, Narusaka Y, Narusaka M, Zhu J K, Shinozaki K: Comparative genomics in salt tolerance between *Arabidopsis* and *Arabidopsis*-related halophyte salt cress using *Arabidopsis* microarray. *Plant Physiol* 2004, 135(3):1697-709
52. Doebley J: Genetics, development and plant evolution. *Curr Opin Genet Dev* 1993, 3(6):865-72
53. Garris A J, Tai T H, Coburn J, Kresovich S, McCouch S: Genetic structure and diversity in *Oryza sativa* L. *Genetics* 2005, 169(3):1631-8
54. Droc G, Ruiz M, Larmande P, Pereira A, Piffanelli P, Morel J B, Dievart A, Courtois B, Guiderdoni E, Perin C: OryGenesDB: a database for rice reverse genetics. *Nucleic Acids Res* 2006, 34 (Database issue):D736-40
55. Fitzgerald H A, Canlas P E, Chem M S, Ronald P C: Alteration of TGA factor activity in rice results in enhanced tolerance to *Xanthomonas oryzae* pv. *oryzae*. *Plant J* 2005, 43(3):335-47.

56. Pfaffl M W: A new mathematical model for relative quantification in real-time RT-PCR. *Nucleic Acids Res* 2001, 29(9):e45.

57. Suzuki R and Shimodaira H: Pvclust: an R package for assessing the uncertainty in hierarchical clustering. *Bioinformatics* 2006 22(12): 1540-42.

The invention claimed is:

1. A genetically modified plant which overexpresses a p33 kD protein comprising an expression cassette encoding the p33 kD protein comprising SEQ ID NO: 2 or a protein having greater than 95% sequence identity with SEQ ID NO: 2 and having an effect on pathogen resistance when overexpressed in the plant, said plant overexpressing said protein and exhibiting an increased resistance to pathogens as compared to a plant that does not overexpress said protein, and wherein said overexpression results from introduction into the plant, or a cell thereof of the expression cassette.

2. The plant of claim 1, wherein said expression cassette comprises a nucleic acid encoding the p33 kD protein comprising SEQ ID NO: 2.

3. The plant of claim 1, wherein said plant is a cereal selected from the group consisting of rice, wheat, sorghum, oat, rye, barley and maize.

4. A transgenic seed of the plant of claim 1, said seed comprising an expression cassette encoding the p33 kD protein comprising SEQ ID NO: 2 or a protein having greater than 95% sequence identity with SEQ ID NO: 2 and having an effect on pathogen resistance when overexpressed in the plant, said seed producing a plant overexpressing said protein and exhibiting an increased resistance to pathogens as compared to a plant that does not overexpress said protein.

5. A transgenic plant, or a descendant of a transgenic plant grown from the seed of claim 4, said transgenic plant or descendant of a transgenic plant grown from said seed comprising an expression cassette encoding the p33 kD protein comprising SEQ ID NO: 2 or a protein having greater than 95% sequence identity with SEQ ID NO: 2 and having an effect on pathogen resistance when overexpressed in the plant, said plant overexpressing said protein and exhibiting an increased resistance to pathogens as compared to a plant that does not overexpress said protein.

6. A method for producing a transgenic plant having increased resistance to a pathogen as compared to a plant that does not overexpress said protein, wherein the method comprises the following steps:
  (a) introducing into a cell of said plant a nucleic acid construct comprising a nucleic acid sequence encoding a p33 kD protein comprising the amino acid sequence set forth in SEQ ID NO: 2 or a protein having above 95% sequence identity with said protein under the control of a constitutive promoter enabling the expression of said nucleic acid sequence;
  (b) optionally; selecting the cell of step (a) which express the p33 kD protein or a protein having above 95% sequence identity with SEQ ID NO: 2;
  (c) regenerating a plant from the cell of step (a) or (b); and
  (d) optionally, selecting a plant of (c) with increased resistance to a pathogen as compared to a plant that does not overexpress said protein.

7. The method of claim 6, wherein the nucleic acid construct comprises a nucleic acid sequence encoding a p33 kD protein comprising SEQ ID NO: 2.

8. The method of claim 6, wherein the transgenic plant is a cereal selected from the group consisting of rice, wheat, barley, oat, rye, sorghum and maize.

9. The method of claim 6, wherein said pathogen is selected from *Magnaporthe, Puccinia, Aspergillus, Ustilago, Rhizoctonia, Septoria, Erisyphe* or *Fusarium* species.

10. The method of claim 9, wherein the pathogen is *Magnaporthe oryzae*.

11. A construct comprising a nucleic acid sequence encoding a p33 kD protein, comprising the amino acid sequence set forth in SEQ ID NO: 2 or a protein having above 95% sequence identity with SEQ ID NO: 2 and having an effect on pathogen resistance when overexpressed in the plant, operably linked to a heterologous promoter functional in a plant, said promoter being a constitutive plant promoter, a plant tissue-specific promoter, a plant development-stage-specific promoter, an inducible promoters or a viral promoter.

12. The construct of claim 11, wherein said p33 kD protein comprises SEQ ID NO: 2.

13. A recombinant vector comprising the construct of claim 11.

14. A cell or plant transformed with the construct of claim 11, said construct comprising a nucleic acid sequence encoding a p33 kD protein comprising the amino acid sequence set forth in SEQ ID NO: 2 or a protein having above 95% sequence identity with SEQ ID NO: 2 and having an effect on pathogen resistance when overexpressed in the plant, operably linked to a heterologous promoter functional in a plant, said promoter being a constitutive plant promoter, a plant tissue-specific promoter, a plant development-stage-specific promoter, an inducible promoters or a viral promoter.

15. A cell or plant transformed with a vector according to claim 13, said vector comprising a construct comprising a nucleic acid sequence encoding a p33 kD protein comprising the amino acid sequence set forth in SE ID NO: 2 or a protein having above 95% sequence identity with SEQ ID NO: 2 and having an effect on pathogen resistance when overexpressed in the plant, operably linked to a heterologous promoter functional in a plant, said promoter being a constitutive plant promoter, a plant tissue-specific promoter, a plant development-stage-specific promoter, an inducible promoters or a viral promoter.

16. A transgenic seed of the plant of claim 14, said seed comprising a construct comprising a nucleic acid sequence encoding a p33 kD protein comprising the amino acid sequence set forth in SEQ ID NO: 2 or a protein having above 95% sequence identity with SEQ ID NO: 2, said seed producing a plant having increased resistance to a pathogen as compared to a plant that does not overexpress said protein.

17. A method for conferring or increasing resistance to pathogens in a plant, wherein the method comprises the following steps:
  (a) introducing into a cell of said plant a nucleic acid construct comprising a nucleic acid sequence encoding a p33 kD protein comprising the amino acid sequence set forth in SEQ ID NO: 2 or a protein having above 95% sequence identity with said protein under the control of a constitutive promoter enabling the expression of said nucleic acid sequence;
(b) optionally, selecting the cells of step (a) which express a p33 kD protein or said protein having above 95% sequence identity with SEQ ID NO: 2;
(c) regenerating a plant from the cell of step (a) or (b); and
(d) optionally, selecting a plant of (c) with increased resistance to a pathogen as compared to a plant that does not overexpress said protein.

18. The method of claim 17, wherein said nucleic acid construct comprises a nucleic acid sequence encoding a p33 kD protein comprising SEQ ID NO: 2.

* * * * *

SEQUENCE LISTING

<160> NUMBER OF SEQ ID NOS: 61

<210> SEQ ID NO 1

<211> LENGTH: 798
<212> TYPE: DNA
<213> ORGANISM: Oryza sp.
<220> FEATURE:
<221> NAME/KEY: misc_feature
<223> OTHER INFORMATION: p33kD; Os03g16950.1

<400> SEQUENCE: 1

```
atggcattca gtagcaaagc ttgccgttgc ttggtgctca tgtcatttgc cttgctccca        60
ctgagcatgg ccatggactc cattggcagc tactgttcag ggaacagctt ggccggcaac       120
agcaaggccg tggcaagcat caactccgtc ctcaccgacc tcgtcgccaa gggctccacc       180
ggcggcggct tcgccacgtc ctccgccggg aaagccaaca acgtcatcta cggtctcgcg       240
caatgccgcg gcgacgtctc caccagcgac tgccaggcct gcctcgcctc cgccgccaac       300
cagatcctca ccagctgcaa ctaccaatcc gactcaagaa tatggtatga ctactgcttc       360
atgcggttcg agaacgagaa cttcatcggg cagacggaca cagatgccgg ggtgattctt       420
gtgaacgtgc aggcgatgga taacggcaag gcgttccaga aggcggtagg gaaggttatg       480
ggcaaggcaa cgtcgcaggc atcacaggct gggagtggtg ggctgggtag gacgaaggat       540
cagtacacgc cgttcatcaa catctacggg ctggcacagt gcacacagga cttgtcaccg       600
ctggcttgcg cacagtgtct gtcaacggcg gtgtcaaggt tcggtcaata ctgcggcgca       660
caacagggat gtcagattaa ctacagtagc tgcagggtgc gctacgagat ctatcccttc       720
tacttcccgc tcgccaccag cgcacgcagc gccaccactg acatgaccaa gtacaccaag       780
atcgttgtgc accgctaa                                                     798
```

<210> SEQ ID NO 2
<211> LENGTH: 265
<212> TYPE: PRT
<213> ORGANISM: Oryza sp.
<220> FEATURE:
<221> NAME/KEY: MISC_FEATURE
<223> OTHER INFORMATION: p33kD; Os03g16950.1

<400> SEQUENCE: 2

```
Met Ala Phe Ser Ser Lys Ala Cys Arg Cys Leu Val Leu Met Ser Phe
1               5                   10                  15

Ala Leu Leu Pro Leu Ser Met Ala Met Asp Ser Ile Gly Ser Tyr Cys
            20                  25                  30

Ser Gly Asn Ser Leu Ala Gly Asn Ser Lys Ala Val Ala Ser Ile Asn
        35                  40                  45

Ser Val Leu Thr Asp Leu Val Ala Lys Gly Ser Thr Gly Gly Gly Phe
    50                  55                  60

Ala Thr Ser Ser Ala Gly Lys Ala Asn Asn Val Ile Tyr Gly Leu Ala
65                  70                  75                  80

Gln Cys Arg Gly Asp Val Ser Thr Ser Asp Cys Gln Ala Cys Leu Ala
                85                  90                  95

Ser Ala Ala Asn Gln Ile Leu Thr Ser Cys Asn Tyr Gln Ser Asp Ser
            100                 105                 110

Arg Ile Trp Tyr Asp Tyr Cys Phe Met Arg Phe Glu Asn Glu Asn Phe
        115                 120                 125

Ile Gly Gln Thr Asp Thr Asp Ala Gly Val Ile Leu Val Asn Val Gln
    130                 135                 140

Ala Met Asp Asn Gly Lys Ala Phe Gln Lys Ala Val Gly Lys Val Met
145                 150                 155                 160

Gly Lys Ala Thr Ser Gln Ala Ser Gln Ala Gly Ser Gly Gly Leu Gly
```

```
                165                 170                 175
Arg Thr Lys Asp Gln Tyr Thr Pro Phe Ile Asn Ile Tyr Gly Leu Ala
            180                 185                 190

Gln Cys Thr Gln Asp Leu Ser Pro Leu Ala Cys Ala Gln Cys Leu Ser
            195                 200                 205

Thr Ala Val Ser Arg Phe Gly Gln Tyr Cys Gly Ala Gln Gly Cys
210                 215                 220

Gln Ile Asn Tyr Ser Ser Cys Arg Val Arg Tyr Glu Ile Tyr Pro Phe
225                 230                 235                 240

Tyr Phe Pro Leu Ala Thr Ser Ala Arg Ser Ala Thr Thr Asp Met Thr
                245                 250                 255

Lys Tyr Thr Lys Ile Val Val His Arg
            260                 265

<210> SEQ ID NO 3
<211> LENGTH: 798
<212> TYPE: DNA
<213> ORGANISM: artificial
<220> FEATURE:
<223> OTHER INFORMATION: SynOs33kD TaMod
<220> FEATURE:
<221> NAME/KEY: misc_feature
<223> OTHER INFORMATION: SynOs33kD TaMod

<400> SEQUENCE: 3
atggcgttct ccagcaaggc ctgccggtgc ctcgtgctga tgtccttcgc gctcctgccg      60
ctcagcatgg cgatggactc catcggcagc tactgctccg caacagcct ggccggcaac      120 tccaaggctg tcgcgtccat caacagcgtg ctcaccgacc tggtcgcgaa gggcagcacc     180
ggcggcggct tcgctacctc cagcgctggc aaggcgaaca acgtgatcta cggcctggcc     240
caatgcaggg gcgacgtctc caccagcgac tgccaggctt gcctcgcgtc cgctgcgaac     300
caaatcctga ccagctgcaa ctaccagtcc gacagccgga tctggtacga ctactgcttc     360
atgaggttcg agaacgagaa cttcatcggc caaaccgaca ccgacgcggg cgtgatcctc     420
gtgaacgtcc aagcgatgga caacggcaag gcgttccaga aggccgtggg caaggtcatg     480
ggcaaggcca cctcccaagc cagccaggct ggctccggcg cctcggcag gaccaaggac      540 caatacaccc ccttcatcaa catctacggc ctggcccagt gcacccagga cctcagccca     600
ctggcctgcg ctcagtgcct ctccaccgcg gtgagccgct cggccaata ctgcggcgcc      660 caacagggct gccagatcaa ctactccagc tgcagggtcc gctacgagat ctacccattc     720
tacttcccgc tggccaccte cgctaggagc gctaccaccg acatgaccaa gtacaccaag    780
atcgtggtcc accggtga                                                  798

<210> SEQ ID NO 4
<211> LENGTH: 263
<212> TYPE: PRT
<213> ORGANISM: Arabidopsis sp.
<220> FEATURE:
<221> NAME/KEY: MISC_FEATURE
<223> OTHER INFORMATION: p33kD

<400> SEQUENCE: 4

Met Lys Thr Leu Val Val Lys Cys Phe Leu Leu Leu Ala Leu Val Cys
1               5                   10                  15

Ser Cys Arg Ala Ala Asp Ser Ile Trp Gln Leu Cys Asn Thr Asn Ser
            20                  25                  30

Asn Ile Ser Ala Ser Ser Gln Val Ser Lys Asn Ile Asp Ser Leu Leu
```

```
            35                  40                  45
Ala Thr Leu Val Ser Lys Thr Pro Ser Lys Gly Phe Lys Thr Thr Thr
 50                  55                  60

Ser Ser Ser Tyr Asn Asn Lys Glu Lys Val Tyr Gly Leu Ala Gln Cys
 65                  70                  75                  80

Arg Gly Asp Ile Ser Asn Thr Asp Cys Ser Thr Cys Ile Gln Asp Ala
                     85                  90                  95

Ala Lys Lys Ile Arg Glu Val Cys Gln Asn Gln Ser Asp Ser Arg Ile
                100                 105                 110

Leu Tyr Asp Phe Cys Phe Leu Arg Tyr Ser Gln Glu Asn Phe Ile Gly
                115                 120                 125

Lys Leu Asp Thr Gly Ala Gly Leu Ile Tyr Phe Asn Val Ala Asn Val
                130                 135                 140

Thr Glu Ile Asp Pro Lys Lys Phe Asp Asn Leu Gly Ala Leu Phe
145                 150                 155                 160

Asp Lys Ile Arg Ser Glu Ala Val Leu Pro Lys Asn Lys Gly Leu Gly
                165                 170                 175

Lys Gly Lys Thr Lys Leu Thr Pro Phe Val Thr Leu Asn Gly Leu Val
                180                 185                 190

Gln Cys Thr Arg Asp Leu Ser Glu Leu Asp Cys Ala Gln Cys Phe Ala
                195                 200                 205

Thr Ala Val Gly Ser Phe Met Thr Thr Cys His Asn Lys Lys Gly Cys
 210                 215                 220

Arg Val Leu Tyr Ser Ser Cys Tyr Val Arg Tyr Glu Phe Tyr Pro Phe
 225                 230                 235                 240

Tyr Phe Pro Leu Asp Pro Ala Lys Thr Gly Pro Ser Val Gly Arg Ile
                245                 250                 255

Ser Ser Val His Leu Ser Pro
                260

<210> SEQ ID NO 5
<211> LENGTH: 268
<212> TYPE: PRT
<213> ORGANISM: Zea mays

<400> SEQUENCE: 5

Met Glu Ser Ser Arg Met Arg Cys Cys Met Leu Leu Val Val Ser Leu
 1                   5                  10                  15

Ala Leu Leu Leu Pro Leu Gly Met Ala Ala Asp Ser Ile Gly Ser Tyr
                 20                  25                  30

Cys Ser Gly Ser Ser Tyr Ala Gly Ser Ser Lys Ala Val Ala Asn Ile
                 35                  40                  45

Asn Ser Val Leu Ala Asp Leu Val Ala Ser Ala Ser Thr Gly Gly
 50                  55                  60

Tyr Ala Thr Ser Thr Ala Gly Lys Gly Asn Asn Ser Ile Ile Tyr Gly
 65                  70                  75                  80

Leu Ala Gln Cys Arg Gly Asp Val Ser Ala Ser Asp Cys Ala Ser Cys
                 85                  90                  95

Leu Ala Asp Ala Ala Lys Gln Leu Pro Ser Thr Cys Ser Tyr Ser Ser
                100                 105                 110

Asp Ala Arg Ile Trp Tyr Asp Tyr Cys Phe Met Arg Tyr Glu Asn Ala
                115                 120                 125

Asn Phe Phe Gly Gln Ala Asp Thr Asp Ala Gly Val Ile Leu Val Asn
                130                 135                 140
```

```
Val Gln Ala Met Asp Asn Pro Lys Ala Phe Glu Lys Ala Val Gly Lys
145                 150                 155                 160

Val Met Gly Lys Ala Thr Ala Gln Ala Ser Ala Ala Gly Ser Ala Gly
            165                 170                 175

Leu Gly Arg Asp Lys Glu Gln Tyr Thr Pro Phe Val Ser Ile Tyr Gly
            180                 185                 190

Leu Ala Gln Cys Thr Arg Asp Leu Ala Pro Leu Thr Cys Ala Gln Cys
            195                 200                 205

Leu Ser Thr Ala Leu Ser Arg Phe Gly Asp Tyr Cys Gly Ala Gln Gln
            210                 215                 220

Gly Cys Gln Ile Asn Tyr Ser Ser Cys Arg Val Arg Tyr Glu Ile Tyr
225                 230                 235                 240

Pro Phe Tyr Phe Pro Leu Ala Gly Lys Gly Gly Leu Ala Thr Thr
                245                 250                 255

Asp Met Thr Lys Asn Thr Lys Ile Val Val Arg Pro
            260                 265

<210> SEQ ID NO 6
<211> LENGTH: 276
<212> TYPE: PRT
<213> ORGANISM: sorghum
<220> FEATURE:
<221> NAME/KEY: MISC_FEATURE
<223> OTHER INFORMATION: p33kD

<400> SEQUENCE: 6

Met Gly Met Ile His Thr Pro Tyr Thr Met Lys Phe Ser Thr Met Arg
1               5                   10                  15

Cys Cys Val Leu Leu Val Ser Leu Ala Leu Leu Pro Leu Gly Met Ala
            20                  25                  30

Ala Asp Ser Ile Gly Ser Tyr Cys Ser Gly Ser Arg Tyr Ala Gly Ser
            35                  40                  45

Asn Lys Ala Val Thr Ser Ile Asn Ser Val Leu Ala Asp Leu Val Ala
        50                  55                  60

Thr Ala Ser Thr Gly Gly Tyr Ala Thr Ser Thr Ala Gly Lys Gly
65                  70                  75                  80

Asn Asn Ile Ile Tyr Gly Leu Ala Gln Cys Arg Gly Asp Val Ser Ala
                85                  90                  95

Ser Asp Cys Ala Ala Cys Leu Ala Asp Ala Ala Lys Gln Leu Pro Ser
            100                 105                 110

Thr Cys Ser Tyr Ser Ser Asp Ala Arg Ile Trp Tyr Asp Tyr Cys Phe
            115                 120                 125

Met Arg Tyr Glu Asn Ala Asp Phe Phe Gly Gln Ala Asp Thr Gly Ala
            130                 135                 140

Gly Val Ile Leu Val Asn Val Gln Ala Met Asp Asn Pro Lys Ala Phe
145                 150                 155                 160

Glu Lys Ala Val Gly Lys Val Ile Gly Lys Ala Thr Ala Gln Ala Ser
            165                 170                 175

Ala Ala Gly Ser Ala Gly Leu Gly Arg Asp Lys Asp Gln Tyr Thr Pro
            180                 185                 190

Phe Val Ser Ile Tyr Gly Leu Ala Gln Cys Thr Arg Asp Leu Ala Pro
            195                 200                 205

Leu Thr Cys Ala Gln Cys Leu Ser Thr Ala Val Ser Arg Phe Gly Asp
            210                 215                 220

Tyr Cys Gly Ala Gln Gln Gly Cys Gln Ile Asn Tyr Ser Ser Cys Arg
225                 230                 235                 240
```

```
Val Arg Tyr Glu Ile Tyr Pro Phe Tyr Pro Leu Ala Gly Asn Gly
            245                 250                 255

Gly Ala Gly Gly Arg Ala Thr Thr Asp Met Thr Lys Asn Thr Lys Ile
            260                 265                 270

Ile Val His Pro
        275

<210> SEQ ID NO 7
<211> LENGTH: 264
<212> TYPE: PRT
<213> ORGANISM: Barley
<220> FEATURE:
<221> NAME/KEY: MISC_FEATURE
<223> OTHER INFORMATION: p33kD

<400> SEQUENCE: 7

Met Ala Leu Cys Arg Ala Arg Ser Gly Leu Leu Val Ala Met Ala
1               5                   10                  15

Leu Leu Pro Leu Gly Met Ala Met Asp Ala Ile Gly Ser Asn Cys Ala
                20                  25                  30

Gly Thr Arg Tyr Ala Ala Gly Ser Gly Lys Gly Asn Ile Asp Ser Val
            35                  40                  45

Leu Ala Asp Leu Val Ala Lys Gly Ser Ser Gly Gly Phe Ala Thr Ser
    50                  55                  60

Ile Ala Gly Lys Gly Asn Ser Thr Val Val Tyr Gly Leu Ala Gln Cys
65                  70                  75                  80

Arg Gly Asp Val Ser Ala Ser Asp Cys Ser Ala Cys Leu Val Asp Ala
                85                  90                  95

Ala Lys Gln Leu Pro Ala Ala Cys Ser Tyr Leu Ser Asp Ala Ile Ile
            100                 105                 110

Trp Tyr Asp Phe Cys Phe Met Arg Tyr Asp Asn Thr Asp Phe Val Gly
        115                 120                 125

His Ser Asp Thr Gly Ala Gly Val Ile Leu Val Asn Val Gln Ala Ala
    130                 135                 140

Asp Asp Pro Lys Pro Phe Lys Thr Ala Val Gly Lys Val Met Asn Lys
145                 150                 155                 160

Ala Thr Ala Lys Ser Ser Ala Ser Gly Ser Ala Gly Leu Gly Arg Ser
                165                 170                 175

Lys Tyr Gln Tyr Thr Pro Phe Val Thr Ile Tyr Gly Leu Ala Gln Cys
            180                 185                 190

Thr Arg Asp Leu Ala Pro Leu Ala Cys Ala Gln Cys Val Ser Val Ala
        195                 200                 205

Leu Ser Lys Phe Gly Asp Tyr Cys Gly Ala Gln Gln Gly Cys Gln Ile
    210                 215                 220

Asn Tyr Ser Ser Cys Arg Val Arg Tyr Glu Ile Tyr Pro Phe Tyr Phe
225                 230                 235                 240

Pro Leu Asp Gly Ala Ala Asn Gly Arg Ala Thr Thr Asp Met Thr Lys
                245                 250                 255

Tyr Thr Lys Ile Val Val His Ala
            260

<210> SEQ ID NO 8
<211> LENGTH: 22
<212> TYPE: DNA
<213> ORGANISM: artificial
<220> FEATURE:
<223> OTHER INFORMATION: MAGGY Taqman probe
```

-continued

<400> SEQUENCE: 8
tgagcagcca acgccgccac aa                                             22

<210> SEQ ID NO 9
<211> LENGTH: 24
<212> TYPE: DNA
<213> ORGANISM: artificial
<220> FEATURE:
<223> OTHER INFORMATION: ACTIN Taqman probe

<400> SEQUENCE: 9
atcacgccca gcaaggtcga gacg                                           24

<210> SEQ ID NO 10
<211> LENGTH: 21
<212> TYPE: DNA
<213> ORGANISM: artificial
<220> FEATURE:
<223> OTHER INFORMATION: ACTIN forward primer

<400> SEQUENCE: 10
gcgtggacaa agttttcaac c                                              21

<210> SEQ ID NO 11
<211> LENGTH: 22
<212> TYPE: DNA
<213> ORGANISM: artificial
<220> FEATURE:
<223> OTHER INFORMATION: ACTIN  reverse primer

<400> SEQUENCE: 11
tctggtaccc tcatcaggca tc                                             22

<210> SEQ ID NO 12
<211> LENGTH: 24
<212> TYPE: DNA
<213> ORGANISM: artificial
<220> FEATURE:
<223> OTHER INFORMATION: BURP forward primer

<400> SEQUENCE: 12
cggctggcta tcatgttatc atcg                                           24

<210> SEQ ID NO 13
<211> LENGTH: 24
<212> TYPE: DNA
<213> ORGANISM: Artificial
<220> FEATURE:
<223> OTHER INFORMATION: BURP reverse primer

<400> SEQUENCE: 13
agttggttta tttcgggaca gagg                                           24

<210> SEQ ID NO 14
<211> LENGTH: 22
<212> TYPE: DNA
<213> ORGANISM: Artificial
<220> FEATURE:
<223> OTHER INFORMATION: PBZ1 forward primer

<400> SEQUENCE: 14
cctgccgaat acgcctaaga tg                                             22

<210> SEQ ID NO 15

```
<211> LENGTH: 24
<212> TYPE: DNA
<213> ORGANISM: Artificial
<220> FEATURE:
<223> OTHER INFORMATION: PBZ1 reverse primer

<400> SEQUENCE: 15
agaacacatt cagacttgcc tctc                                          24

<210> SEQ ID NO 16
<211> LENGTH: 18
<212> TYPE: DNA
<213> ORGANISM: Artificial
<220> FEATURE:
<223> OTHER INFORMATION: PR5 forward primer

<400> SEQUENCE: 16
cgctgccccg acgcttac                                                 18

<210> SEQ ID NO 17
<211> LENGTH: 23
<212> TYPE: DNA
<213> ORGANISM: Artificial
<220> FEATURE:
<223> OTHER INFORMATION: PR5 reverse primer

<400> SEQUENCE: 17
gacgacttgg tagttgctgt tgc                                           23

<210> SEQ ID NO 18
<211> LENGTH: 24
<212> TYPE: DNA
<213> ORGANISM: Artificial
<220> FEATURE:
<223> OTHER INFORMATION: GLUC forward primer

<400> SEQUENCE: 18
cgttccatat atagttgtgg tttg                                          24

<210> SEQ ID NO 19
<211> LENGTH: 24
<212> TYPE: DNA
<213> ORGANISM: Artificial
<220> FEATURE:
<223> OTHER INFORMATION: GLUC reverse primer

<400> SEQUENCE: 19
tcaagttcat attatttgtc tctg                                          24

<210> SEQ ID NO 20
<211> LENGTH: 18
<212> TYPE: DNA
<213> ORGANISM: Artificial
<220> FEATURE:
<223> OTHER INFORMATION: POX223 forward primer

<400> SEQUENCE: 20
acgacgccca acgccttc                                                 18

<210> SEQ ID NO 21
<211> LENGTH: 21
<212> TYPE: DNA
<213> ORGANISM: Artificial
<220> FEATURE:
<223> OTHER INFORMATION: POX223 reverse primer

<400> SEQUENCE: 21
```

-continued cttccagcaa cgaacgcatc c                    21

<210> SEQ ID NO 22
<211> LENGTH: 23
<212> TYPE: DNA
<213> ORGANISM: Artificial
<220> FEATURE:
<223> OTHER INFORMATION: SPL7 forward primer

<400> SEQUENCE: 22
cggattagag gcttgcgtgt tac                    23

<210> SEQ ID NO 23
<211> LENGTH: 23
<212> TYPE: DNA
<213> ORGANISM: Artificial
<220> FEATURE:
<223> OTHER INFORMATION: SPL7 reverse primer

<400> SEQUENCE: 23
gcacagtagt cagcggatag aac                    23

<210> SEQ ID NO 24
<211> LENGTH: 21
<212> TYPE: DNA
<213> ORGANISM: Artificial
<220> FEATURE:
<223> OTHER INFORMATION: CHI forward primer

<400> SEQUENCE: 24
ccagacggga cggaggttta c                    21

<210> SEQ ID NO 25
<211> LENGTH: 20
<212> TYPE: DNA
<213> ORGANISM: Artificial
<220> FEATURE:
<223> OTHER INFORMATION: CHI reverse primer

<400> SEQUENCE: 25
agatgcgtgt gcgaccaagg                    20

<210> SEQ ID NO 26
<211> LENGTH: 21
<212> TYPE: DNA
<213> ORGANISM: Artificial
<220> FEATURE:
<223> OTHER INFORMATION: 33KDA forward primer

<400> SEQUENCE: 26
gccaccactg acatgaccaa g                    21

<210> SEQ ID NO 27
<211> LENGTH: 22
<212> TYPE: DNA
<213> ORGANISM: Artificial
<220> FEATURE:
<223> OTHER INFORMATION: 33KDA reverse primer

<400> SEQUENCE: 27
acgctgaaac atccacagac ac                    22

<210> SEQ ID NO 28
<211> LENGTH: 20
<212> TYPE: DNA

```
<213> ORGANISM: Artificial
<220> FEATURE:
<223> OTHER INFORMATION: NPR1 forward primer

<400> SEQUENCE: 28
cctgatggtt gccttctgtc                                                  20

<210> SEQ ID NO 29
<211> LENGTH: 24
<212> TYPE: DNA
<213> ORGANISM: Artificial
<220> FEATURE:
<223> OTHER INFORMATION: NPR1 reverse primer

<400> SEQUENCE: 29
attcaagcac ttgtattaca cctc                                             24

<210> SEQ ID NO 30
<211> LENGTH: 21
<212> TYPE: DNA
<213> ORGANISM: Artificial
<220> FEATURE:
<223> OTHER INFORMATION: HSP90 forward primer

<400> SEQUENCE: 30
cctcctcctc ctcctcctca c                                                21

<210> SEQ ID NO 31
<211> LENGTH: 21
<212> TYPE: DNA
<213> ORGANISM: Artificial
<220> FEATURE:
<223> OTHER INFORMATION: HSP90 reverse primer

<400> SEQUENCE: 31
ggacacctca gcctggaact c                                                21

<210> SEQ ID NO 32
<211> LENGTH: 22
<212> TYPE: DNA
<213> ORGANISM: Artificial
<220> FEATURE:
<223> OTHER INFORMATION: SUB forward primer

<400> SEQUENCE: 32
cggaaagttg ctgacccatt cg                                               22

<210> SEQ ID NO 33
<211> LENGTH: 19
<212> TYPE: DNA
<213> ORGANISM: Artificial
<220> FEATURE:
<223> OTHER INFORMATION: SUB reverse primer

<400> SEQUENCE: 33
gctcgccgca ccttgattg                                                   19

<210> SEQ ID NO 34
<211> LENGTH: 23
<212> TYPE: DNA
<213> ORGANISM: Artificial
<220> FEATURE:
<223> OTHER INFORMATION: EDS5 forward primer

<400> SEQUENCE: 34
cacggctagg ttcagttcca atg                                              23
```

<210> SEQ ID NO 35
<211> LENGTH: 24
<212> TYPE: DNA
<213> ORGANISM: Artificial
<220> FEATURE:
<223> OTHER INFORMATION: EDS5 reverse primer

<400> SEQUENCE: 35
ccaatccatc agcaagaaga gacg                                          24

<210> SEQ ID NO 36
<211> LENGTH: 23
<212> TYPE: DNA
<213> ORGANISM: Artificial
<220> FEATURE:
<223> OTHER INFORMATION: EDR1 forward primer

<400> SEQUENCE: 36
atgggtggac ctgtgaaaga tgc                                           23

<210> SEQ ID NO 37
<211> LENGTH: 21
<212> TYPE: DNA
<213> ORGANISM: Artificial
<220> FEATURE:
<223> OTHER INFORMATION: EDR1 reverse primer

<400> SEQUENCE: 37
agtagggcac ggtgacgaga c                                             21

<210> SEQ ID NO 38
<211> LENGTH: 20
<212> TYPE: DNA
<213> ORGANISM: Artificial
<220> FEATURE:
<223> OTHER INFORMATION: CEBIP forward primer

<400> SEQUENCE: 38
cacttgtacg gctgcttgaa                                               20

<210> SEQ ID NO 39
<211> LENGTH: 20
<212> TYPE: DNA
<213> ORGANISM: Artificial
<220> FEATURE:
<223> OTHER INFORMATION: CEBIP reverse primer

<400> SEQUENCE: 39
ggaaggtggg aagtccattc                                               20

<210> SEQ ID NO 40
<211> LENGTH: 23
<212> TYPE: DNA
<213> ORGANISM: Artificial
<220> FEATURE:
<223> OTHER INFORMATION: RCI1 forward primer

<400> SEQUENCE: 40
caatttgagt tgtgccaatg agc                                           23

<210> SEQ ID NO 41
<211> LENGTH: 22
<212> TYPE: DNA
<213> ORGANISM: Artificial
<220> FEATURE:

<223> OTHER INFORMATION: RCI1 reverse primer

<400> SEQUENCE: 41
ctgtgttagc cattccttga cg                                    22

<210> SEQ ID NO 42
<211> LENGTH: 24
<212> TYPE: DNA
<213> ORGANISM: Artificial
<220> FEATURE:
<223> OTHER INFORMATION: RBBI2 forward primer

<400> SEQUENCE: 42
atctgtgtcc gtcaataaaa ctcg                                  24

<210> SEQ ID NO 43
<211> LENGTH: 21
<212> TYPE: DNA
<213> ORGANISM: Artificial
<220> FEATURE:
<223> OTHER INFORMATION: RBBI2 reverse primer

<400> SEQUENCE: 43
ttgctcttgg tcactggcta g                                     21

<210> SEQ ID NO 44
<211> LENGTH: 23
<212> TYPE: DNA
<213> ORGANISM: Artificial
<220> FEATURE:
<223> OTHER INFORMATION: MAPK6 forward primer

<400> SEQUENCE: 44
gccgttcaat atggtgtttc aag                                   23

<210> SEQ ID NO 45
<211> LENGTH: 22
<212> TYPE: DNA
<213> ORGANISM: Artificial
<220> FEATURE:
<223> OTHER INFORMATION: MAPK6 reverse primer

<400> SEQUENCE: 45
gccttatatc tgggtggatg gg                                    22

<210> SEQ ID NO 46
<211> LENGTH: 18
<212> TYPE: DNA
<213> ORGANISM: Artificial
<220> FEATURE:
<223> OTHER INFORMATION: GNS1 forward primer

<400> SEQUENCE: 46
cagagggctt ggcttgcg                                         18

<210> SEQ ID NO 47
<211> LENGTH: 18
<212> TYPE: DNA
<213> ORGANISM: Artificial
<220> FEATURE:
<223> OTHER INFORMATION: GNS1 reverse primer

<400> SEQUENCE: 47
gcctaccaca gcgtaccg                                         18

-continued

```
<210> SEQ ID NO 48
<211> LENGTH: 19
<212> TYPE: DNA
<213> ORGANISM: Artificial
<220> FEATURE:
<223> OTHER INFORMATION: LTP2 forward primer

<400> SEQUENCE: 48
gacatcgcag gccgtacat                                                    19

<210> SEQ ID NO 49
<211> LENGTH: 21
<212> TYPE: DNA
<213> ORGANISM: Artificial
<220> FEATURE:
<223> OTHER INFORMATION: LTP2 reverse primer

<400> SEQUENCE: 49
catgcatcga tctagcagca a                                                 21

<210> SEQ ID NO 50
<211> LENGTH: 23
<212> TYPE: DNA
<213> ORGANISM: Artificial
<220> FEATURE:
<223> OTHER INFORMATION: HLHDB forward primer

<400> SEQUENCE: 50
ggttttgaaa catgatcctg ctg                                               23

<210> SEQ ID NO 51
<211> LENGTH: 24
<212> TYPE: DNA
<213> ORGANISM: Artificial
<220> FEATURE:
<223> OTHER INFORMATION: HLHDB reverse primer

<400> SEQUENCE: 51
aggtacattg acaaggagat atgg                                              24

<210> SEQ ID NO 52
<211> LENGTH: 21
<212> TYPE: DNA
<213> ORGANISM: Artificial
<220> FEATURE:
<223> OTHER INFORMATION: ZnFg1 forward primer

<400> SEQUENCE: 52
gcggtgttgt atgtagctgg t                                                 21

<210> SEQ ID NO 53
<211> LENGTH: 20
<212> TYPE: DNA
<213> ORGANISM: Artificial
<220> FEATURE:
<223> OTHER INFORMATION: ZnFg1 reverse primer

<400> SEQUENCE: 53
gtctcagcgt acggttcaca                                                   20

<210> SEQ ID NO 54
<211> LENGTH: 24
<212> TYPE: DNA
<213> ORGANISM: Artificial
<220> FEATURE:
<223> OTHER INFORMATION: ZnFgXS forward primer
```

```
<400> SEQUENCE: 54
tgagtgatga ctatgattct gatg                                          24

<210> SEQ ID NO 55
<211> LENGTH: 19
<212> TYPE: DNA
<213> ORGANISM: Artificial
<220> FEATURE:
<223> OTHER INFORMATION: ZnFgXS reverse primer

<400> SEQUENCE: 55
ttctctgtga cgcttgacc                                                19

<210> SEQ ID NO 56
<211> LENGTH: 21
<212> TYPE: DNA
<213> ORGANISM: Artificial
<220> FEATURE:
<223> OTHER INFORMATION: ZnFg2 forward primer

<400> SEQUENCE: 56
ctgcgtaccc tctccatctg a                                             21

<210> SEQ ID NO 57
<211> LENGTH: 19
<212> TYPE: DNA
<213> ORGANISM: Artificial
<220> FEATURE:
<223> OTHER INFORMATION: ZnFg2 reverse primer

<400> SEQUENCE: 57
tggcagcctc ttcgttgtt                                                19

<210> SEQ ID NO 58
<211> LENGTH: 24
<212> TYPE: DNA
<213> ORGANISM: Artificial
<220> FEATURE:
<223> OTHER INFORMATION: OsKS4 forward primer

<400> SEQUENCE: 58
tacggttggt tgttagagaa gacg                                          24

<210> SEQ ID NO 59
<211> LENGTH: 24
<212> TYPE: DNA
<213> ORGANISM: Artificial
<220> FEATURE:
<223> OTHER INFORMATION: OsKS4 reverse primer

<400> SEQUENCE: 59
ccattcatag cacccatcat ttcc                                          24

<210> SEQ ID NO 60
<211> LENGTH: 23
<212> TYPE: DNA
<213> ORGANISM: Artificial
<220> FEATURE:
<223> OTHER INFORMATION: EIN2 forward primer

<400> SEQUENCE: 60
gcaacaagga accagtgaca acc                                           23

<210> SEQ ID NO 61
<211> LENGTH: 21
```

```
<212> TYPE: DNA
<213> ORGANISM: Artificial
<220> FEATURE:
<223> OTHER INFORMATION: EIN2 reverse primer

<400> SEQUENCE: 61
gcagtcgtct ccgcagttag g                                      21
```